United States Patent [19]

Greene et al.

[11] Patent Number: 5,919,764
[45] Date of Patent: Jul. 6, 1999

[54] COMPOUNDS THAT BIND TO P185 AND METHODS OF USING THE SAME

[75] Inventors: Mark I. Greene, Penn Valley; Xin Zhang, Philadelphia, both of Pa.

[73] Assignee: The Trustees of the University of Pennsylvania, Philadelphia, Pa.

[21] Appl. No.: 08/922,048

[22] Filed: Sep. 2, 1997

Related U.S. Application Data

[62] Division of application No. 08/433,318, May 3, 1995, Pat. No. 5,663,144.

[51] Int. Cl.$^6$ .............................. A61K 38/03; C07K 4/00
[52] U.S. Cl. .............................. 514/14; 514/15; 530/326; 530/327; 530/328; 424/1.11
[58] Field of Search .................................. 530/324, 325, 530/326, 327, 328, 329; 514/12, 13, 14, 15; 424/1.11

[56] References Cited

U.S. PATENT DOCUMENTS

| | | | |
|---|---|---|---|
| 5,200,178 | 4/1993 | Strauss et al. | 424/1.1 |
| 5,367,060 | 11/1994 | Vandlen et al. | 530/399 |
| 5,464,751 | 11/1995 | Greene et al. | 435/7.23 |
| 5,663,144 | 9/1997 | Greene et al. | 514/14 |

OTHER PUBLICATIONS

Rudinger, J 'Characteristics of amino acids as components of peptide hormones sequence' in Peptide Hormones, (ed. J.A. Parsons). University Park Press, Baltimore, pp. 1–7 1976.
Bach, A. et al., "Structural Studies of Family of High Affinity LIgands for GP$^{IIb/IIIa}$", New Adv. Peptidomimetics Small Mol. Design 1994, 1, 1–26.
Bargmann, C. et al., "The Neu Oncogene Encodes an Epidermal Growth Factor Receptor–Related Protein", Nature 1986, 319, 226–230.
Bargmann, C. and Weinberg, R., "Increased tyrosine kinase activity associated with the protein encoded by the activated neu oncogene", Proc. Natl. Acad. Sci. USA 1988, 85, 5394–5398.
Bookman, M.A. et al., "Immunotoxins Directed Against c–erbB2: Limited Activity Due to Poor Internalization", 3rd International Symposium on Immunotoxins, 1992, p. 15.
Di Blasio et al., "Noncoded Residues as Building Block in the Design of Specific Secondary Structures: Symmetrically Disubstituted Glycines and β–Alanine", Biopolymers 1993, 33, 1037–1049.
Dougall, W. et al., "Modulation of p185–$^{c-erB-2}$ Expression and Tumorigenic Growth by Anti–receptor Monoclonal Antibodies", J. of Cellular Biochem. 1994, Supplement 18D, No. Y 507, p. 252.
Drebin et al., "Down–Modulation of an Oncogene Protein Product and Reversion of the Transformed Phenotype by Monoclonal Antibodies", Cell 1985, 41, 695–706.
Drebin, J. et al., "Inhibition of Tumor Growth by a Monoclonal Antibody reactive with an Oncogene–Encoded Tumor Antigen", PNAS USA 1986, 83, 9129–9133.

Drebin, J. et al., "Monoclonal Antibodies Reactive with Distinct Domains of the Neu Oncogene–Encoded p185 Molecule Exert Synergistic Anti–Tumor Effects in Vivo", Oncogene 1988, 2, 273–277.
Hruby, V.J. et al., "Conformational and Topographical Considerations in the Design of Biologically Active Peptides", Biopolymers 1993, 33, 1073–1082.
Lodato, R.F. et al., "Immunohistochemical Evaluation of c–erbB–2 Oncogene Expression in Ductal Carcinoma In Situ and Atypical Ductal Hyperplasia of the Breast", Modern Pathol. 1990, 3(4), 449–454.
Manning,M. et al., "Design of cyclic and linear peptide antagonists of vasopression and oxytocin: current status and future directions", Regulatory Peptides 1993, 45, 279–283.
Matsuyama, T. et al., A Novel Extracellular Cyclic Lipopeptide Which Promotes Glagellum–Dependent and –Independent Spreading Growth of Serratia marcescens, J. of Bacteriology 1992, 174, 1769–1776.
Saragovi, H. et al., "Design and Synthesis of a Mimetic from an Antibody Complementarity–determining Region", Science, 1991, 253, 792–795.
Saragovi, H., "Constrained Peptides and Mimetics as Probes of Protein Secondary Structure", Immunomethods 1992, 1, 5–9.
Slamon, D.J., "Role of the HEr–2/neu Gene in Human Breast and Ovarian Cancer", Meeting of the American Association of Clinical Research, 1992.
Wada, T. et al., "Anti–receptor Antibodies Reverse the Phenotype of Cells Transformed by Two Interacting Protooncogene Encoded Receptor Proteins", Oncogene 1990, 5, 489–495.
Wood, S. and Wetzel, "Novel Cyclization Chemistry Especially Suited for Biologically Derived, Unprotected Peptides", Int. J. Peptide Protein Res. 1992, 39, 533–539.
Wright, C. et al., "Expression of c–erbB–2 Oncoprotein: A Prognostic Indicator in Human Breast Cancer", Cancer Research 1989, 49, 2087–2090.
Berge, et al., "Pharmaceutical Salts", J. Pharm. Sci., 66, 1977, 1–19.
Zabrecky, et al., "The Extracellular Domain of p185/neu Is Release from the Surface of Human Breast Carcinoma Cells, SK–BR–3", J. Biol. Chem., 256, 1991, 1716–1720.

Primary Examiner—Cecilia J. Tsang
Assistant Examiner—Anish Gupta
Attorney, Agent, or Firm—Pennie & Edmonds LLP

[57] ABSTRACT

Novels peptides and pharmaceutical compositions comprising the same are disclosed. Conjugated compositions peptides linked to detectable agents and/or cytotoxic agents. are disclosed. Method of detecting tumors that have p185 on tumor cell surfaces are disclosed. Methods of preventing transformation of a normal cell into a tumor cell in an individual at risk of developing a tumor having tumor cells which have p185 on their surfaces are disclosed. Methods of treating an individual who has cancer characterized by tumor cells that have a p185 on their cell surfaces are disclosed.

18 Claims, No Drawings

COMPOUNDS THAT BIND TO P185 AND METHODS OF USING THE SAME

This is a divisional of application Ser. No. 08/433,318, filed May 3, 1995 now U.S. Pat. No. 5,663,144.

ACKNOWLEDGEMENT OF GOVERNMENT RIGHTS

This invention was made with Government support under 5 R01 CA55306 awarded by the National Institutes of Health. The Government has certain rights in this invention.

FIELD OF THE INVENTION

The invention relates to compounds useful for and methods of treating individuals suspected of suffering from tumors and preventing tumors in individuals suspected of being susceptible to the development of tumors and for detecting and imaging tumors.

BACKGROUND OF THE INVENTION

Significant amounts of time and money have been spent to better understand cancer and searching for ways to prevent and cure cancer. The results of these research efforts have provided a greater understanding of the biological and biochemical events that participate in the formation of tumors.

Malignant cells display a variety of characteristics that distinguish them from normal cells. Recent studies in the molecular genetics of cancer indicate that certain genes known as oncogenes may play a role in the transformation of some cells from their normal condition to a cancerous condition. Proto-oncogenes, genes closely related to these genes, are found in somatic cells of all eukaryotic species examined and have been highly conserved in evolution; it is thought that proto-oncogenes normally play critical roles in cellular growth and development. Oncogene amplification and chromosomal rearrangements involving oncogenes have been detected in a large number of tumors. Furthermore some tumors have been shown to contain activated oncogenes which, in DNA transfection assays, are capable of conferring neoplastic properties upon non-neoplastic rodent fibroblast cell lines. Collectively these studies suggest that alterations in proto-oncogene structure and function play a critical role in the development of neoplasia.

Although most oncogene-encoded proteins reside in the nucleus or the cytoplasm, some oncogenes encode proteins that are present as antigenic sites on the cell surface. For example, the erbB-1, erbB-2, erbB-3, erbB-4, fms and ros oncogene products are transmembrane glycoproteins that possess extracellular domains. The sis oncogene product may also exist in a membrane associated form on the surface of transformed cells.

Another oncogene which encodes a protein that exposes antigenic sites on the surface of transformed cells has been identified by transfection of DNA from ethyl nitrosourea-induced rat neuroblastomas into NIH3T3 cells. This oncogene has been termed neu. The homologous human gene is called erbB-2. The erbB-2 gene has been found to be amplified or overexpressed in some human tumors, particularly those of the breast, suggesting that this gene may play an imported role in the etiology of human cancer.

The protein encoded by the erbB-2 oncogene is a 185 kDa transmembrane glycoprotein with tyrosine kinase activity, generally known by the name p185. The erbB-2 gene is closely related to the epidermal growth factor (EGF) receptor gene in structure.

The erbB-2 oncogene and p185 has also been found active in human adenocarcinomas including breast, lung, salivary gland and kidney adenocarcinomas, as well as prostate neuroblastoma. In human primary breast cancers, amplification of the erbB-2 oncogene was found in about 30% of all malignant tumors examined. Increased stage of malignancy, characterized by large tumor size and increased number of positive lymph nodes as well as reduced survival time and decreased time to relapse, was directly correlated with an increased level of amplification of the erbB-2 gene. The erbB-2 protooncogene is expressed at low levels in normal human tissues. Further, erbB-2 has been associated with 100% of the ductal carcinomas studied in situ, Lodato, R. F., et al. (1990) *Modern Pathol.* 3(4):449.

Current treatments for individuals suffering from carcinomas expressing amplified levels of erbB-2 include surgery, radiation therapy, chemotherapy, immunotherapy and, usually, combinations of two or more of such therapies. Despite advances made in these fields, the mortality rate among individuals suffering from cancer remains unacceptable high. Complete tumor eradication and total remission is not always the outcome.

There remains a need for additional modalities in the anti-tumor approaches and for additional methods of reducing and/or eliminating tumors in individuals. There is a need for anti-tumor agents which can be administered as therapeutics to individuals suffering form tumors, particularly tumors with amplified levels of p185.

While changes in diet and behavior can reduce the likelihood of developing cancer, it has been found that some individuals have a higher risk of developing cancer than others. Further, those individuals who have already developed cancer and who have been effectively treated face a risk of relapse and recurrence.

Advancements in the understanding of genetics and developments in technology as well as epidemiology allow for the determination of probability and risk assessment an individual has for developing cancer. Using family health histories and/or genetic screening, it is possible to estimate the probability that a particular individual has for developing certain types of cancer. Those individuals that have been identified as being predisposed to developing a particular form of cancer can take only limited prophylactic steps towards reducing the risk of cancer. There is no currently available method or composition which can chemically intervene with the development of cancer and reduce the probability a high risk individual will develop cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

There is a need for improved preventative agents for individual with a high risk to develop cancer and for individuals who have had cancer enter remission or be removed. In cases where the type of cancer the individual is at risk to develop, such as tumors associated with erbB-2, there is a need for specific agents which can be administered to reduce the probability that a predisposed individual will develop cancer or that a patient in remission will suffer a relapse.

There is a need for therapeutic compositions useful to treat individuals identified as having p185-associated tumors. There is a need to develop prophylactic compositions for individuals susceptible to developing p185-associated tumors.

SUMMARY OF THE INVENTION

The present invention relates to peptides having the formula:

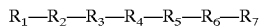

wherein:
- $R_1$ is 1–6 amino acid residues and at least one of which is tyrosine or phenylalanine;
- $R_2$ is a linking moiety which bonds with $R_1$, $R_3$ and $R_6$ such that a portion of said peptide is cyclicized;
- $R_3$ is 0–20 amino acids;
- $R_4$ is 6 amino acids;
- $R_5$ is 0–20 amino acids;
- $R_6$ is a linking moiety which bonds with $R_5$, $R_7$ and $R_2$ such that a portion of said peptide is cyclicized;
- $R_7$ is 1–6 amino acid residues and at least one of which is tyrosine or phenylalanine;

wherein:
- $R_1$, $R_2$, $R_3$, $R_4$, $R_5$, $R_6$ and $R_7$, taken together, are 30 amino acids or less;

and $R_4$ is has the formula:

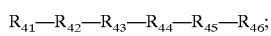

wherein:
either,
- $R_{41}$ is E or D;
- $R_{42}$ is N or Q;
- $R_{43}$ is W;
- $R_{44}$ is D or E;
- $R_{45}$ is W; and,
- $R_{46}$ is Y or F;

or
- $R_{41}$ is G, V, A, I or L;
- $R_{42}$ is D or E;
- $R_{43}$ is G, V, A, I or L;
- $R_{44}$ is F or Y;
- $R_{45}$ is Y or F; and,
- $R_{46}$ is A, I, L, G or V.

The present invention relates to conjugated compositions that comprise such peptides linked to detectable agents and/or cytotoxic agents.

The present invention relates to methods of detecting a tumor that has p185 on tumor cell surfaces. The methods comprise the step of administering, to an individual suspected of having such a tumor or being susceptible to such a tumor, a conjugated composition that comprises such peptides linked to detectable agents and detecting the presence of localized conjugated composition within the body of the individual.

The present invention relates to pharmaceutical compositions which comprise such peptides and/or conjugated compositions in combination with a pharmaceutically acceptable carrier or diluent.

The present invention relates to methods of preventing transformation of a normal cell into a tumor cell in an individual at risk of developing a tumor having tumor cells which have p185 on their surfaces. The method comprises the steps of: identifying such an individual; and administering to the individual such peptides.

The present invention relates to methods of treating an individual who has cancer characterized by tumor cells that have a p185 on their cell surfaces. The methods comprise the steps of: identifying such an individual; and administering to the individual, a therapeutically effective amount of such peptides and/or conjugated compositions.

DETAILED DESCRIPTION OF THE INVENTION

As used herein, the terms "neu-associated cancer", "erbB-2-associated cancer", "neu-associated tumors", "erbB-2-associated tumors", "p185-mediated tumors" and "p185-associated tumors" are meant to refer to tumor cells and neoplasms which express the erbB-2 gene to produce p185. Examples of erbB-2-associated cancer include many human adenocarcinomas. Breast, ovary, lung, pancreas, salivary gland and kidney adenocarcinomas and prostate, and some neuroblastoma have been found to be erbB-2-associated cancers.

When a therapeutically effective amount of a compound of the invention is administered to an individual who has erbB-2-associated cancer, the effect is that the proliferation rate of tumor cells is slowed down or eliminated. As used herein, the term "compound" is meant to refer to a peptide or a peptide mimetic which is useful in the method of detecting, imaging, treating or preventing p185-mediated tumors.

As used herein, the term "therapeutically effective amount" is meant to refer to an amount of a compound which produces a medicinal effect observed as reduction or reverse in tumorigenic phenotype of tumor cells in an individual when a therapeutically effective amount of a compound is administered to an individual who is susceptible to or suffering from p185-mediated tumors. Therapeutically effective amounts are typically determined by the effect they have compared to the effect observed when a composition which includes no active ingredient is administered to a similarly situated individual.

As used herein, the term "high risk individual" is meant to refer to an individual who has had a erbB-2-associated tumor either removed or enter remission and who is therefore susceptible to a relapse or recurrence. As part of a treatment regimen for a high risk individual, the individual can be prophylactically treated to conduct the recurrence of the erbB-2-associated tumors. Thus, once it is known that an individual has had cancer characterized by tumor cells with p185 on their cell surfaces, the individual can be treated according to the present invention to prevent normal cells from transforming into tumor cells.

As used herein, the term "preventing the development of tumors" is meant to refer to preventing the transformation of normal cells into tumor cells. Thus, the development of tumors refers to the transformation event which results in the loss of a normal phenotype and the acquisition of a transformed phenotype. According to some aspects of the present invention, compounds may be administered to individuals who are at risk of developing tumors. The prophylactic administration of compounds of the invention to high risk individuals results in the prevention of the transformation event occurring. Cells having the normal phenotype are not converted to the cells having transformed phenotype. The compounds of the invention prevent tumors before they are formed by preventing a normal ell from becoming a cancer cell.

As used herein, the term prophylactically effective amount" is meant to refer to an amount of a compound which produces a medicinal effect observed as the prevention of non-transformed cells from becoming transformed in an individual when a prophylactically effective amount of a compound is administered to an individual who is susceptible to p185-mediated tumors. Prophylactically effective amounts are typically determined by the effect they have compared to the effect observed when a composition which includes no active ingredient is administered to a similarly situated individual.

As used herein, the terms "conformationally restricted peptides", "constrained peptides" and "conformationally constrained peptides" are used interchangeably and are meant to refer to peptides which, for example through intramolecular bonds, are conformationally stable and remain in a sufficiently restricted conformation. The compounds have an affinity to p185 and, when bound to p185 as cells, a biologically active effect on cells that have a p185-mediated transformation phenotype.

As used herein, the terms "aromatic amino acids" and "aromatic amino acid residues" used interchangeably are meant to refer to phenylalanine and tyrosine.

As used herein, the term "exocyclic amino acid residue" is meant to refer to amino acid residues which are linked to cyclicized peptide but which are not within the portion of the peptide that makes up the circularized structure.

As used herein, the term "exocyclic portions" is meant to refer to an amino acid sequence having one or more amino acid residues which is linked to cyclicized peptide but which are not within the portion of the peptide that makes up the circularized structure.

As used herein, the term "linking moiety" is meant to refer to a molecular component or functional group which is capable of forming bonds with three amino acids.

As used herein, the term "linking amino acid residue" is meant to refer to an amino acid residue that is a linking moiety.

As used herein, the terms "active sequence" and "active region" are used interchangeably and are meant to refer to the amino acid sequence of the portion of a compound of the invention that is directly interacts with p185, wherein the interaction is characterized by an affinity between the active portion and p185.

The present invention relates to constrained peptides that contain exocyclic portions including exocyclic amino acids that are aromatic amino acids as well as an active region which specifically binds to p185. Co-pending U.S. Ser. No. 08/257,783 filed Jun. 10, 1994 and entitled "Constrained Peptides" is incorporated herein by reference in its entirety.

The present invention is useful to therapeutically treat an individual identified as suffering from erbB-2-associated tumors in order to reverse the transformed phenotype of the tumor cells. The present invention is useful to prophylactically treat an individual who is predisposed to develop erbB-2-associated tumors or who has had erbB-2-associated tumors and is therefore susceptible to a relapse or recurrence. The present invention is useful to detectably image tumors with respect to p185 on their surfaces. The present invention is useful to detect and quantify p185 on all surfaces.

The translation product of the erbB-2 oncogene is p185, a transmembrane glycoprotein having tyrosine kinase activity and a molecular weight of about 185,000 daltons as determined by carrying out electrophoresis on the glycoprotein and comparing its movement with marker proteins of known molecular weight. Experiments have shown that p185 forms homodimers with other p185 molecules or heterodimers with epidermal growth factor receptor (EGFR) and that these dimers exhibit elevated tyrosine kinase activity which brings about the transformed phenotype in cells having such dimers. It is believed that dimerization of p185 with other membrane bound receptors, such as other p185 molecules or EGFR, results in elevated levels of tyrosine kinase activity and the transformed phenotype.

According to the present invention, compounds bind to p185 and thereby prevent the dimerization with other membrane bound receptors by down modulation of their surface receptors. When bound to p185, the compounds of the invention induce internalization of the receptor which results in elimination or reduction of tyrosine kinase activity. The elimination or reduction of tyrosine kinase activity results in an elimination or reduction in cell proliferation levels and a non-transformed, quiescent phenotype. The compounds of the invention cause down-modulation of erbB-2 cell surface reception. When bound to p185, the compounds of the invention reverse the transformed state of such cells, resulting in decreasing the rate of transformation in cells showing intact non-activated tyrosine kinase receptors found in normal cells are not affected by the compounds of the invention and hence are non-toxic.

The compounds of the invention are therefore useful in the treatment of individuals suspected of having from p185-mediated tumors. When administered to individuals who have been thusly identified, the compounds of the invention bind to p185, thereby causing modulation of erbB-2 receptors. The p185 receptor bound to the compound internalize and the internalization of the p185 receptor contributes to the decrease in tyrosine kinase activity of the p185 receptors. When the tyrosine kinase activity in the cell is reduced from the elevated levels associated with amplified or overexpressed p185, the cell becomes quiescent and displays a non-transformed phenotype.

The compounds of the invention are also useful in the prevention of p185-mediated tumor formation and therefore in the method of prophylactically treating high risk individuals from developing p185-mediated tumors. That is, the prophylactic administration of compounds of the invention results in the prevention of cells that over express p185 from becoming transformed. The cells in the individuals which would turn into tumors in an untreated individual never become transformed and never become tumors in individuals treated by the methods of the invention. When administered to individuals who have been identified as being susceptible to or otherwise at risk of developing tumors, the compounds of the invention bind to p185, thereby preventing and cause the internalization of the receptor/compound complex. The p185 receptor bound to the compound internalizes and the bound p185 receptor does not contribute the elevation in tyrosine kinase activity associated with dimerized p185 receptors. The tyrosine kinase activity in the cell never become sufficiently elevated and the cell remains non-transformed.

The compounds of the invention can be labelled or otherwise made detectable. As a detectable compound that binds to p185, the compounds are useful as imaging agents and reagents in diagnostic procedures that are used to identify a tumor as being a p185-associated tumor. Labelled compounds of the invention can be administered to individuals suspected of suffering from p185-associated tumors. The labelled compounds will bind to the high density of p185 on cells and thereby accumulate on p185-associated tumor cells. Using standard imaging techniques, the site of the tumors can be detected.

One aspect of the invention therefore relates to methods of imaging p185-associated tumors. Such methods comprise the steps of administering a detectable compound of the invention to an individuals who is suffering from or susceptible to erbB-2-associated cancer and detecting the location of the detectable compound within the body of the individual.

The compounds bind to p185 that is present on cell surfaces and are therefore useful as diagnostic/characterizing reagents in diagnostic kits. When a tissue sample from an individual is contacted with a compound of the invention, the compound will bind to the p185 present on cells. The level of p185 expression can be quantified. Labelled compounds of the invention are also useful as in vitro reagents to quantify the amount of p185 present in the cell. Such information indicates whether or not a tumor is p185 mediated and therefore, whether specific treatments should be used or avoided. Using standard techniques, samples believed to include tumor cells are obtained and contacted with labelled compounds of the active region of the invention. After removing any unbound labelled compounds, the quantity of labelled compound bound to the cell or the quantity of removed as unbound labelled compounds is determined. The information directly relates to the amount of p185 the cell expresses and thus can be used to determine whether a cell is over expressing p185. Overexpression of p185 indicates p185-mediated transformation. This information is useful in formulating the prognosis and course of treatment to be imposed on the individual. Kits of the invention comprise detectable compounds of the invention and instructions for performing assays of the invention. Optionally, kits may also contain one or more of the following: containers which comprise positive controls, containers which comprise negative controls, photographs of representative examples of positive results and photographs of representative examples of negative results.

According to some embodiments, the present invention provides peptides having the formula:

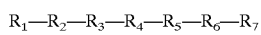
$$R_1-R_2-R_3-R_4-R_5-R_6-R_7$$

wherein:
$R_1$ is 1–6 amino acid residues and at least one of which is tyrosine or phenylalanine;
$R_2$ is a linking moiety which bonds with $R_1$, $R_3$ and $R_6$ such that a portion of the molecule is cyclicized;
$R_3$ is 0–20 amino acids;
$R_4$ is 6 amino acids;
$R_5$ is 0–20 amino acids;
$R_6$ is a linking moiety which bonds with $R_5$, $R_7$ and $R_2$ such that a portion of the molecule is cyclicized;
$R_7$ is 1–6 amino acid residues and at least one of which is tyrosine or phenylalanine;
wherein:
$R_1$, $R_2$, $R_3$, $R_4$, $R_5$, $R_6$ and $R_7$, taken together, are 30 amino acids or less;
and $R_4$ is has the formula:

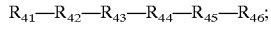
$$R_{41}-R_{42}-R_{43}-R_{44}-R_{45}-R_{46};$$

wherein:
either,
$R_{41}$ is E or D;
$R_{42}$ is N or Q;
$R_{43}$ is W;
$R_{44}$ is D or E;
$R_{45}$ is W; and,
$R_{46}$ is Y or F;
or
$R_{41}$ is G, V, A, I or L;
$R_{42}$ is D or E;
$R_{43}$ is G, V, A, I or L;
$R_{44}$ is F or Y;
$R_{45}$ is Y or F; and,
$R_{46}$ is A, I, L, G or V;

The primary function of $R_1$ in compounds of the present invention arises from the presence of at least one amino acid that contains an aromatic group: i.e. the presence of tyrosine or phenylalanine. The presence of the aromatic amino acid at position $R_1$ results in an increase affinity of the peptide to p185 and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_1$ are disclosed in co-pending U.S. Ser. No. 08/257,783. In some embodiments, the additional amino acids are present as a site for linkage to detectable labels or moieties. In some embodiments, the additional amino acids are present as a site for dimerization with other peptides; either for formation of homodimers with each other or heterodimers with other peptides. In some preferred embodiments, $R_1$ is 1–5 amino acids. In some preferred embodiments, $R_1$ is 4 amino acids. In some preferred embodiments, $R_1$ is 3 amino acids. In some preferred embodiments, $R_1$ is 2 amino acids. In some preferred embodiments, $R_1$ is 1 amino acid. In some preferred embodiments, $R_1$ comprises F-E. In some preferred embodiments, $R_1$ consists of F-E. In some preferred embodiments, $R_1$ comprises Y-E. In some preferred embodiments, $R_1$ consists of Y-E. In some preferred embodiments, $R_1$ comprises F. In some preferred embodiments, $R_1$ consists of F. In some preferred embodiments, $R_1$ comprises Y. In some preferred embodiments, $R_1$ consists of Y. Other examples of $R_1$ include F-K-T-N-K (SEQ ID NO:1) and F-G-Q. Contemplated equivalents include aromatic functional groups at $R_1$ which are not part of tyrosine or phenylalanine.

The function of $R_2$ is to form bonds with $R_1$ as well as to form bonds with $R_6$ which cyclicize or otherwise conformationally restrict the molecule. Bonds between $R_2$ and $R_6$ cyclicize the molecule and thereby maintain $R_3-R_4-R_5$, and, specifically $R_4$, in a constrained conformation which produces the specific biologically active surface that has an affinity for and interacts with p185. Further, in such an arrangement $R_1$ becomes an exocyclic portion of the peptide. Accordingly, $R_2$ may be any moiety capable of forming bonds with $R_6$ as well as $R_1$ and $R_3$. $R_2$ is preferably an amino acid residue, most preferably cysteine. When both $R_2$ and $R_6$ are cysteine, the disulfide bonds form between the two cysteines cyclicize the molecule. It is wcontemplated that $R_2$ may any moiety that, together with $R_6$, will allow for the cyclization of the portion of the molecule that includes $R_1-R_2-R_3-R_4-R_5-R_6$ while rendering $R_1$ and $R_7$ exocyclic portions of the peptide. Those having ordinary skill in the art can readily prepare peptides according to the present invention in which $R_2$ and $R_6$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers*, 33:1037–1049; Wood, et al., (1992) *J. Pep. Prot. Res.*, 39:533–539; Saragovi, et al., (1992) *Immunomethods*, 1:5–9; Saragovi, et al., (1991) *Science*, 253:792–795; Manning, et al., (1993) *Reg. Peptides*, 45:279–283; Hruby, (1993) *Biopolymers*, 33:1073–1082; Bach, et al., (1994) *New Adv. Peptidomimetics Small Mol. Design*, I:1–26; and Matsuyama, et al., (1992) *J. Bacteriol.*, 174:1769–1776, each of which are incorporated herein by reference.

The function of $R_3$ is to serve as spacers and provide structure to present the active region in proper conformation. In some embodiments, the cyclization of the active region by particular linking moieties results in the proper. folding of the active region to place it in active conformation and no $R_3$ is required. In some embodiments, the cyclization of the active region by particular linking moieties requires additional spacing and turns to facilitate that proper folding of the active region in order to place it in active conformation. In such embodiments, amino acid residues or sequences may be provided at $R_3$. In some preferred embodiments, $R_3$ is 0–10 amino acids. In some preferred embodiments, $R_3$ is 0–5 amino acids. In some preferred embodiments, $R_3$ is 0 amino acids.

$R_4$ is the active region of the compounds according to this aspect of the invention. In compounds of the invention, the functional groups of the active region are in a conformation which places them in a particular three dimensional arrangement that allows them to interact with the amino acids and functional groups thereon of p185 and to bind to p185 through such interactions. In peptide mimetics, the functional groups are provided in the active three dimensional arrangement but are connected to modified or different backbones.

In some preferred embodiments, $R_4$ is E-N-W-D-W-Y (SEQ ID NO:2), D-N-W-D-W-Y (SEQ ID NO:3), E-Q-W-D-W-Y (SEQ ID NO:4), D-Q-W-D-W-Y (SEQ ID NO:5), E-N-W-E-W-Y (SEQ ID NO:6), D-N-W-E-W-Y (SEQ ID NO:7), E-Q-W-E-W-Y (SEQ ID NO:8), D-Q-W-E-W-Y (SEQ ID NO:9), E-N-W-D-W-F (SEQ ID NO:10), D-N-W-D-W-F (SEQ ID NO:11), E-Q-W-D-W-F (SEQ ID NO:12), D-Q-W-D-W-F (SEQ ID NO:13), E-N-W-E-W-F (SEQ ID NO:14), D-N-W-E-W-F (SEQ ID NO:15), E-Q-W-E-W-F (SEQ ID NO:16) or D-Q-W-E-W-F (SEQ ID NO:17). In some preferred embodiments, $R_4$ is E-N-W-D-W-Y (SEQ ID NO:2).

In some preferred embodiments, $R_4$ is G/V/A/I/L-D/E-G/V/A/I/L-F/Y-Y/F-A/G/V/I/L (SEQ ID NO:18). It is possible to vary each residue with one that contributes equivalent bulk and hydrophobic moment and that still permits hydrogen bonding to surrounding water molecules or to residues to which the compound attaches. SEQ ID NO:18 represents a formula for defining each of the permutations of possible variations in sequence within the scope of the invention. In some preferred embodiments, $R_4$ is G-D-G-F-Y-A (SEQ ID NO:19), G-E-G-F-Y-A (SEQ ID NO:20), G-D-G-Y-Y-A (SEQ ID NO:21), G-E-G-Y-Y-A (SEQ ID NO:22), G-D-G-F-F-A (SEQ ID NO:23), G-E-G-F-F-A (SEQ ID NO:24), G-D-G-Y-F-A (SEQ ID NO:25), G-E-G-Y-F-A (SEQ ID NO:24)) A-D-G-F-Y-A (SEQ ID NO:27), A-E-G-F-Y-A (SEQ ID NO:28), A-D-G-Y-Y-A (SEQ ID NO:29), A-E-G-Y-Y-A (SEQ ID NO:30), A-D-G-F-F-A (SEQ ID NO:31), A-E-G-F-F-A (SEQ ID NO:32), A-D-G-Y-F-A (SEQ ID NO:33), A-E-G-Y-F-A (SEQ ID NO:34), G-D-A-F-Y-A (SEQ ID NO:35), G-E-A-F-Y-A (SEQ ID NO:36), G-D-A-Y-Y-A (SEQ ID NO:37), G-E-A-Y-Y-A (SEQ ID NO:38), G-D-A-F-F-A (SEQ ID NO:39), G-E-A-F-F-A (SEQ ID NO:40), G-D-A-Y-F-A (SEQ ID NO:41), G-E-A-Y-F-A (SEQ ID NO:42), A-D-A-F-Y-A (SEQ ID NO:43), A-E-A-F-Y-A (SEQ ID NO:44), A-D-A-Y-Y-A (SEQ ID NO:45), A-E-A-Y-Y-A (SEQ ID NO:46), A-D-A-F-F-A (SEQ ID NO:47), A-E-A-F-F-A (SEQ ID NO:48), A-D-A-Y-F-A (SEQ ID NO:49), A-E-A-Y-F-A (SEQ ID NO:50), G-D-G-F-Y-G (SEQ ID NO:51), G-E-G-F-Y-G (SEQ ID NO:52), G-D-G-Y-Y-G (SEQ ID NO:53), G-E-G-Y-Y-G (SEQ ID NO:54), G-D-G-F-F-G (SEQ ID NO:55), G-E-G-F-F-G (SEQ ID NO:56), G-D-G-Y-F-G (SEQ ID NO:57), G-E-G-Y-F-G (SEQ ID NO:58), A-D-G-F-Y-G (SEQ ID NO:59), A-E-G-F-Y-G (SEQ ID NO:60), A-D-G-Y-Y-G (SEQ ID NO:61), A-E-G-Y-Y-G (SEQ ID NO:62), A-D-G-F-F-G (SEQ ID NO:63), A-E-G-F-F-G (SEQ ID NO:64), A-D-G-Y-F-G (SEQ ID NO:65), A-E-G-Y-F-G (SEQ ID NO:66), G-D-A-F-Y-G (SEQ ID NO:67), G-E-A-F-Y-G (SEQ ID NO:68), G-D-A-Y-Y-G (SEQ ID NO:69), G-E-A-Y-Y-G (SEQ ID NO:70), G-D-A-F-F-G (SEQ ID NO:71), G-E-A-F-F-G (SEQ ID NO:72), G-D-A-Y-F-G (SEQ ID NO:73), G-E-A-Y-F-G (SEQ ID NO:74), A-D-A-F-Y-G (SEQ ID NO:75), A-E-A-F-Y-G (SEQ ID NO:76), A-D-A-Y-Y-G (SEQ ID NO:77), A-E-A-Y-Y-G (SEQ ID NO:78), A-D-A-F-F-G (SEQ ID NO:79), A-E-A-F-F-G (SEQ ID NO:80), A-D-A-Y-F-G (SEQ ID NO:81), or A-E-A-Y-F-G (SEQ ID NO:82).

The function of $R_5$ is to present the active region in proper conformation. In some embodiments, the cyclization of the active region by particular linking moieties results in the proper folding of the active region to place it in active conformation and no $R_5$ is required. In some embodiments, the cyclization of the active region by particular linking moieties requires additional spacing and turns to facilitate that proper folding of the active region in order to place it in active conformation. In such embodiments, amino acid residues or sequences may be provided at $R_5$. In some preferred embodiments, $R_5$ is 0–10 amino acids. In some preferred embodiments, $R_5$ is 0–5 amino acids. In some preferred embodiments, $R_5$ is 0 amino acids.

The function of $R_6$ is to form bonds with $R_2$ which cyclicize or otherwise conformationally restrict the molecule. Bonds between $R_6$ and $R_2$ cyclicize the molecule and thereby maintain $R_3$—$R_4$—$R_5$, and, specifically $R_4$, in a constrained conformation which produces the specific biologically active surface that has an affinity for and interacts with p185. Accordingly, $R_6$ may be any moiety capable of forming bonds with $R_2$ as well as $R_5$ and $R_7$. $R_6$ is preferably an amino acid residue, most preferably cysteine. When both $R_6$ and $R_2$ are cysteine, disulfide bonds formed between the two cysteines cyclicizes the molecule. It is contemplated that $R_6$ may any moiety that, together with $R_2$, will allow for the cyclization of the molecule. Those having ordinary skill in the art can readily prepare peptides according to the present invention in which $R_2$ and $R_6$ are moieties capable of forming bonds to each other. The cyclization of linear peptides using disulfide bonds between non-adjacent cysteines is well known. Similarly, other non-adjacent amino acid residues may be linked to cyclicize a peptide sequence and the means to do so are similarly well known. Other methods of cyclization include those described by Di Blasio, et al., (1993) *Biopolymers*, 33:1037–1049; Wood, et al., (1992) *J. Pep. Prot. Res.*, 39:533–539; Saragovi, et al., (1992) *Immunomethods*, 1:5–9; Saragovi, et al., (1991) *Science*, 253:792–795; Manning, et al., (1993) *Reg.*

Peptides, 45:279–283; Hruby, (1993) Biopolymers, 33:1073–1082; Bach, et al., (1994) New Adv. Peptidomimetics Small Mol. Design, I:1–26; and Matsuyama, et al., (1992) J. Bacteriol., 174:1769–1776, each of which are incorporated herein by reference.

The primary function of $R_7$ in compounds of the present invention arises from the presence of at least one amino acid that contains an aromatic group: i.e. the presence of tyrosine or phenylalanine. The presence of the aromatic amino acid at position $R_7$ results in an increase affinity of the peptide to p185 and an attendant increase in activity of the compound. In embodiments where additional amino acid residues are present, they can present the aromatic amino acid in a more effective position to further increase the affinity and activity of the compound. Additional amino acids that may be present must not eliminate the effect that the aromatic amino acid has on affinity or activity. Examples of amino acid sequences which may be used as $R_7$ are disclosed in co-pending U.S. Ser. No. 08/257,783. In some embodiments, the additional amino acids are present as a site for linkage to detectable labels eor moieties. In some embodiments, the additional amino acids are present as a site for dimerization with other peptides; either for formation of homodimers with each other or heterodimers with other peptides. In some preferred embodiments, $R_7$ is 1–5 amino acids. In some preferred embodiments, $R_7$ is 4 amino acids. In some preferred embodiments, $R_7$ is 3 amino acids. In some preferred embodiments, $R_7$ is 2 amino acids. In some preferred embodiments, $R_7$ is 1 amino acid. In some preferred embodiments, $R_7$ comprises Y-P-P-G-C (SEQ ID NO:83). In some preferred embodiments, $R_7$ consists of Y-P-P-G-C (SEQ ID NO:83) In some preferred embodiments, $R_7$ comprises Y-M-D-V (SEQ ID NO:84). In some preferred embodiments, $R_7$ consists of Y-M-D-V (SEQ ID NO:84). In some preferred embodiments, $R_7$ comprises F. In some preferred embodiments, $R_7$ consists of F. In some preferred embodiments, $R_7$ comprises F-D-V. In some preferred embodiments, $R_7$ consists of F-D-V. In some preferred embodiments, $R_7$ comprises Y. In some preferred embodiments, $R_7$ consists of Y. Another example of $R_7$ is Q-F. Contemplated equivalents include aromatic functional groups at $R_7$ which are not part of tyrosine or phenylalanine.

In some preferred embodiments, $R_1$ and $R_7$ collectively contain both tyrosine and phenylalanine. That is, if $R_1$ comprises tyrosine then $R_7$ comprises phenylalanine and if $R_1$ comprises phenylalanine then $R_7$ comprises tyrosine. In some preferred embodiments, $R_1$ and $R_7$ do not both contain tyrosine or phenylalanine. That is, if $R_1$ comprises tyrosine and not phenylalanine then $R_7$ comprises phenylalanine and not tyrosine and if $R_1$ comprises phenylalanine and not tyrosine then $R_7$ comprises tyrosine and not phenylalanine.

In some preferred embodiments, $R_1$, $R_2$, $R_3$, $R_4$, $R_5$, $R_6$ and $R_7$, taken together, are less than 30 amino acids. In some preferred embodiments, $R_1$, $R_2$, $R_3$, $R_4$, $R_5$, $R_6$ and $R_7$, taken together, are 20 amino acids or less. In some preferred embodiments, $R_1$, $R_2$, $R_3$, $R_4$, $R_5$, $R_6$ and $R_7$, taken together, are less than 20 amino acids. In some preferred embodiments, $R_1$, $R_2$, $R_3$, $R_4$, $R_5$, $R_6$, and $R_7$, taken together, are 15 amino acids. In some preferred embodiments, $R_1$, $R_2$, $R_3$, $R_4$, $R_5$, $R_6$ and $R_7$, taken together, are less than 15 amino acids. In some preferred embodiments, $R_1$, $R_2$, $R_3$, $R_4$, $R_5$, $R_6$ and $R_7$, taken together, are 14 amino acids. In some preferred embodiments, $R_1$, $R_2$, $R_3$, $R_4$, $R_5$, $R_6$ and $R_7$, taken together, are 13 amino acids. In some preferred embodiments, $R_1$, $R_2$, $R_3$, $R_4$, $R_5$, $R_6$ and $R_7$, taken together, are 12 amino acids. In some preferred embodiments, $R_1$, $R_2$, $R_3$, $R_4$, $R_5$, $R_6$ and $R_7$, taken together, are 11 amino acids.

In some preferred embodiments, $R_1$, $R_2$, $R_3$, $R_4$, $R_5$, $R_6$ and $R_7$, taken together, are 10 amino acids.

In some embodiments, the peptide is selected from the group consisting of: F-E-C-E-N-W-D-W-Y-C-Y-P-P-G-C (SEQ ID NO:85); F-C-G-D-G-F-Y-A-C-M-D-V (SEQ ID NO:86); F-E-C-D-N-W-D-W-Y-C-Y-P-P-G-C (SEQ ID NO:87); F-E-C-E-Q-W-D-W-Y-C-Y-P-P-G-C (SEQ ID NO:88); F-E-C-D-Q-W-D-W-Y-C-Y-P-P-G-C (SEQ ID NO:89); F-E-C-E-N-W-E-W-Y-C-Y-P-P-G-C (SEQ ID NO:90); F-E-C-D-N-W-E-W-Y-C-Y-P-P-G-C (SEQ ID NO:91); F-E-C-E-Q-W-E-W-Y-C-Y-P-P-G-C (SEQ ID NO:92); F-E-C-D-Q-W-E-W-Y-C-Y-P-P-G-C (SEQ ID NO:93); F-E-C-E-N-W-D-W-F-C-Y-P-P-G-C (SEQ ID NO:94); F-E-C-D-N-W-D-W-F-C-Y-P-P-G-C (SEQ ID NO:95); F-E-C-E-Q-W-D-W-F-C-Y-P-P-G-C (SEQ ID NO:96); F-E-C-D-Q-W-D-W-F-C-Y-P-P-G-C (SEQ ID NO:97); F-E-C-E-N-W-E-W-F-C-Y-P-P-G-C (SEQ ID NO:98); F-E-C-D-N-W-E-W-F-C-Y-P-P-G-C (SEQ ID NO:99); F-E-C-E-Q-W-E-W-F-C-Y-P-P-G-C (SEQ ID NO:100); F-E-C-D-Q-W-E-W-F-C-Y-P-P-G-C (SEQ ID NO:101); F-C-E-N-W-D-W-Y-C-Y-P-P-G-C (SEQ ID NO:102); F-C-D-N-W-D-W-Y-C-Y-P-P-G-C (SEQ ID NO:103); F-C-E-Q-W-D-W-Y-C-Y-P-P-G-C (SEQ ID NO:104); F-C-D-Q-W-D-W-Y-C-Y-P-P-G-C (SEQ ID NO:105); F-C-E-N-W-E-W-Y-C-Y-P-P-G-C (SEQ ID NO:106); F-C-D-N-W-E-W-Y-C-Y-P-P-G-C (SEQ ID NO:107); F-C-E-Q-W-E-W-Y-C-Y-P-P-G-C (SEQ ID NO:108); F-C-D-Q-W-E-W-Y-C-Y-P-P-G-C (SEQ ID NO:109); F-C-E-N-W-D-W-F-C-Y-P-P-G-C (SEQ ID NO:110); F-C-D-N-W-D-W-F-C-Y-P-P-G-C (SEQ ID NO:111); F-C-E-Q-W-D-W-F-C-Y-P-P-G-C (SEQ ID NO:112); F-C-D-Q-W-D-W-F-C-Y-P-P-G-C (SEQ ID NO:113); F-C-E-N-W-E-W-F-C-Y-P-P-G-C (SEQ ID NO:114); F-C-D-N-W-E-W-F-C-Y-P-P-G-C (SEQ ID NO:115); F-C-E-Q-W-E-W-F-C-Y-P-P-G-C (SEQ ID NO:116); F-C-D-Q-W-E-W-F-C-Y-P-P-G-C (SEQ ID NO:117); F-E-C-E-N-W-D-W-Y-C-Y (SEQ ID NO:118); F-E-C-D-N-W-D-W-Y-C-Y (SEQ ID NO:119); F-E-C-E-Q-W-D-W-Y-C-Y (SEQ ID NO:120); F-E-C-D-Q-W-D-W-Y-C-Y (SEQ ID NO:121); F-E-C-E-N-W-E-W-Y-C-Y (SEQ ID NO:122); F-E-C-D-N-W-E-W-Y-C-Y (SEQ ID NO:123); F-E-C-E-Q-W-E-W-Y-C-Y (SEQ ID NO:124); F-E-C-D-Q-W-E-W-Y-C-Y (SEQ ID NO:125); F-E-C-E-N-W-D-W-F-C-Y (SEQ ID NO:126); F-E-C-D-N-W-D-W-F-C-Y (SEQ ID NO:127); F-E-C-E-Q-W-D-W-F-C-Y (SEQ ID NO:128); F-E-C-D-Q-W-D-W-F-C-Y (SEQ ID NO:129); F-E-C-E-N-W-E-W-F-C-Y (SEQ ID NO:130); F-E-C-D-N-W-E-W-F-C-Y (SEQ ID NO:131); F-E-C-E-Q-W-E-W-F-C-Y (SEQ ID NO:132); F-E-C-D-Q-W-E-W-F-C-Y (SEQ ID NO:133); F-C-E-N-W-D-W-Y-C-Y (SEQ ID NO:134); F-C-D-N-W-D-W-Y-C-Y (SEQ ID NO:135); F-C-E-Q-W-D-W-Y-C-Y (SEQ ID NO:136); F-C-D-Q-W-D-W-Y-C-Y (SEQ ID NO:137); F-C-E-N-W-E-W-Y-C-Y (SEQ ID NO:138); F-C-D-N-W-E-W-Y-C-Y (SEQ ID NO:139); F-C-E-Q-W-E-W-Y-C-Y (SEQ ID NO:140); F-C-D-Q-W-E-W-Y-C-Y (SEQ ID NO:141); F-C-E-N-W-D-W-F-C-Y (SEQ ID NO:142); F-C-D-N-W-D-W-F-C-Y (SEQ ID NO:143); F-C-E-Q-W-D-W-F-C-Y (SEQ ID NO:144); F-C-D-Q-W-D-W-F-C-Y (SEQ ID NO:145); F-C-E-N-W-E-W-F-C-Y (SEQ ID NO:146); F-C-D-N-W-E-W-F-C-Y (SEQ ID NO:147); F-C-E-Q-W-E-W-F-C-Y (SEQ ID NO:148); F-C-D-Q-W-E-W-F-C-Y (SEQ ID NO:149); F-E-C-D-N-W-D-W-Y-C-Y-P-P-G-C (SEQ ID NO:150); F-E-C-E-Q-W-D-W-Y-C-Y-P-P-G-C (SEQ ID NO:151); F-E-C-D-Q-W-D-W-Y-C-Y-P-P-G-C (SEQ ID NO:152); F-E-C-E-N-W-E-W-Y-C-Y-P-P-G-C (SEQ ID NO:153); F-E-C-D-N-W-E-W-Y-C-Y-P-P-G-C (SEQ ID NO:154); F-E-C-E-Q-W-E-W-Y-C-Y-P-P-

G-C (SEQ ID NO:155); F-E-C-D-Q-W-E-W-Y-C-Y-P-P-G-C (SEQ ID NO:156); F-E-C-E-N-W-D-W-F-C-Y-P-P-G-C (SEQ ID NO:157); F-E-C-D-N-W-D-W-F-C-Y-P-P-G-C (SEQ ID NO:158); F-E-C-E-Q-W-D-W-F-C-Y-P-P-G-C (SEQ ID NO:159); F-E-C-D-Q-W-D-W-F-C-Y-P-P-G-C (SEQ ID NO:160); F-E-C-E-N-W-E-W-F-C-Y-P-P-G-C (SEQ ID NO:161); F-E-C-D-N-W-E-W-F-C-Y-P-P-G-C (SEQ ID NO:162); F-E-C-E-Q-W-E-W-F-C-Y-P-P-G-C (SEQ ID NO:163); F-E-C-D-Q-W-E-W-F-C-Y-P-P-G-C (SEQ ID NO:164); F-C-E-N-W-D-W-Y-C-Y-P-P-G-C (SEQ ID NO:165); F-C-D-N-W-D-W-Y-C-Y-P-P-G-C (SEQ ID NO:166); F-C-E-Q-W-D-W-Y-C-Y-P-P-G-C (SEQ ID NO:167); F-C-D-Q-W-D-W-Y-C-Y-P-P-G-C (SEQ ID NO:168); F-C-E-N-W-E-W-Y-C-Y-P-P-G-C (SEQ ID NO:169); F-C-D-N-W-E-W-Y-C-Y-P-P-G-C (SEQ ID NO:170); F-C-E-Q-W-E-W-Y-C-Y-P-P-G-C (SEQ ID NO:171); F-C-D-Q-W-E-W-Y-C-Y-P-P-G-C (SEQ ID NO:172); F-C-E-N-W-D-W-F-C-Y-P-P-G-C (SEQ ID NO:173); F-C-D-N-W-D-W-F-C-Y-P-P-G-C (SEQ ID NO:174); F-C-E-Q-W-D-W-F-C-Y-P-P-G-C (SEQ ID NO:175); F-C-D-Q-W-D-W-F-C-Y-P-P-G-C (SEQ ID NO:176); F-C-E-N-W-E-W-F-C-Y-P-P-G-C (SEQ ID NO:177); F-C-D-N-W-E-W-F-C-Y-P-P-G-C (SEQ ID NO:178); F-C-E-Q-W-E-W-F-C-Y-P-P-G-C (SEQ ID NO:179); and F-C-D-Q-W-E-W-F-C-Y-P-P-G-C (SEQ ID NO:180).

In some embodiments, compounds of the invention have the formula:

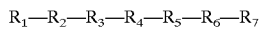

wherein:

$R_1-R_2-R_3$ is F-C, Y-C, F-E-C, or Y-E-C;

$R_4$ is G/V/A/I/L-D/E-G/V/A/I/L-F/Y-Y/F-A/G/V/I/L (SEQ ID NO:18); and $R_5-R_6-R_7$ is C-Y-P-P-G-C (SEQ ID NO:181), C-Y-M-D-V (SEQ ID NO:182), C-F, C-F-D-V (SEQ ID NO:183) or C-Y.

In some embodiments, compounds of the invention have the formula:

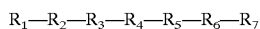

wherein:

$R_1-R_2-R_3$ is F-C, Y-C, F-E-C, or Y-E-C;

$R_4$ is G-D-G-F-Y-A (SEQ ID NO:19), G-E-G-F-Y-A (SEQ ID NO:20), G-D-G-Y-Y-A (SEQ ID NO:21), G-E-G-Y-Y-A (SEQ ID NO:22), G-D-G-F-F-A (SEQ ID NO:23), G-E-G-F-F-A (SEQ ID NO:24), G-D-G-Y-F-A (SEQ ID NO:25), G-E-G-Y-F-A (SEQ ID NO:26), A-D-G-F-Y-A (SEQ ID NO:27), A-E-G-F-Y-A (SEQ ID NO:28), A-D-G-Y-Y-A (SEQ ID NO:29), A-E-G-Y-Y-A (SEQ ID NO:30), A-D-G-F-F-A (SEQ ID NO:31), A-E-G-F-F-A (SEQ ID NO:32), A-D-G-Y-F-A (SEQ ID NO:33), A-E-G-Y-F-A (SEQ ID NO:34), G-D-A-F-Y-A (SEQ ID NO:35), G-E-A-F-Y-A (SEQ ID NO:36), G-D-A-Y-Y-A (SEQ ID NO:37), G-E-A-Y-Y-A (SEQ ID NO:38), G-D-A-F-F-A (SEQ ID NO:39), G-E-A-F-F-A (SEQ ID NO:40), G-D-A-Y-F-A (SEQ ID NO:41), G-E-A-Y-F-A (SEQ ID NO:42), A-D-A-F-Y-A (SEQ ID NO:43), A-E-A-F-Y-A (SEQ ID NO:44), A-D-A-Y-Y-A (SEQ ID NO:45), A-E-A-Y-Y-A (SEQ ID NO:46), A-D-A-F-F-A (SEQ ID NO:47), A-E-A-F-F-A (SEQ ID NO:48), A-D-A-Y-F-A (SEQ ID NO:49), A-E-A-Y-F-A (SEQ ID NO:50), G-D-G-F-Y-G (SEQ ID NO:51), G-E-G-F-Y-G (SEQ ID NO:52), GD-G-Y-Y-G (SEQ ID NO:53), G-E-G-Y-Y-G (SEQ ID NO:54), G-D-G-F-F-G (SEQ ID NO:55), G-E-G-F-F-G (SEQ ID NO:56), G-D-G-Y-F-G (SEQ ID NO:57), G-E-G-Y-F-G (SEQ ID NO:58), A-D-G-F-Y-G (SEQ ID NO:59), A-E-G-F-Y-G (SEQ ID NO:60), A-D-G-Y-Y-G (SEQ ID NO:61), A-E-G-Y-Y-G (SEQ ID NO:62), A-D-G-F-F-G (SEQ ID NO:63), A-E-G-F-F-G (SEQ ID NO:64), A-D-G-Y-F-G (SEQ ID NO:65), A-E-G-Y-F-G (SEQ ID NO:66), G-D-A-F-Y-G (SEQ ID NO:67), G-E-A-F-Y-G (SEQ ID NO:68), G-D-A-Y-Y-G (SEQ ID NO:69), G-E-A-Y-Y-G (SEQ ID NO:70), G-D-A-F-F-G (SEQ ID NO:71), G-E-A-F-F-G (SEQ ID NO:72), G-D-A-Y-F-G (SEQ ID NO:73), G-E-A-Y-F-G (SEQ ID NO:74), A-D-A-F-Y-G (SEQ ID NO:75), A-E-A-F-Y-G (SEQ ID NO:76), A-D-A-Y-Y-G (SEQ ID NO:77), A-E-A-Y-Y-G (SEQ ID NO:78), A-D-A-F-F-G (SEQ ID NO:79), A-E-A-F-F-G (SEQ ID NO:80), A-D-A-Y-F-G (SEQ ID NO:81), or A-E-A-Y-F-G (SEQ ID NO:82); and $R_5-R_6-R_7$ is C-Y-P-P-G-C (SEQ ID NO:181), C-Y-M-D-V (SEQ ID NO:182), C-F, C-F-D-V (SEQ ID NO:183) or C-Y.

Some examples of compounds of the invention include compounds 1–1280.

In compounds 1–64:

$R_1-R_2-R_3$ is F-C, $R_4$ is one of SEQ ID NO:19–SEQ ID NO:82, and $R_5-R_6-R_7$ is C-Y-P-P-G-C (SEQ ID NO:181).

In compounds 65–128:

$R_1-R_2-R_3$ is F-C, $R_4$ is one of SEQ ID NO:19–SEQ ID NO:82, and $R_5-R_6-R_7$ is C-Y-M-D-V (SEQ ID NO:182).

In compounds 129–192:

$R_1-R_2-R_3$ is F-C, $R_4$ is one of SEQ ID NO:19–SEQ ID NO:82, and $R_5-R_6-R_7$ is C-F.

In compounds 193–256:

$R_1-R_2-R_3$ is F-C, $R_4$ is one of SEQ ID NO:19–SEQ ID NO:82, and $R_5-R_6-R_7$ is C-F-D-V (SEQ ID NO:183).

In compounds 257–320:

$R_1-R_2-R_3$ is F-C, $R_4$ is one of SEQ ID NO:19–SEQ ID NO:82, and $R_5-R_6-R_7$ is C-Y.

In compounds 321–384:

$R_1-R_2-R_3$ is Y-C, $R_4$ is one of SEQ ID NO:19–SEQ ID NO:82, and $R_5-R_6-R_7$ is C-Y-P-P-G-C (SEQ ID NO:181).

In compounds 385–448:

$R_1-R_2-R_3$ is Y-C, $R_4$ is one of SEQ ID NO:19–SEQ ID NO:82, and $R_5-R_6-R_7$ is C-Y-M-D-V (SEQ ID NO:182).

In compounds 449–512:

$R_1-R_2-R_3$ is Y-C, $R_4$ is one of SEQ ID NO:19–SEQ ID NO:82, and $R_5-R_6-R_7$ is Y-F.

In compounds 513–576:

$R_1-R_2-R_3$ is Y-C, $R_4$ is one of SEQ ID NO:19–SEQ ID NO:82, and $R_5-R_6-R_7$ is C-F-D-V (SEQ ID NO:183).

In compounds 577–640:

$R_1-R_2-R_3$ is Y-C, $R_4$ is one of SEQ ID NO:19–SEQ ID NO:82, and $R_5-R_6-R_7$ is C-Y.
In compounds 641–704:
$R_1-R_2-R_3$ is F-E-C,
$R_4$ is one of SEQ ID NO:19–SEQ ID NO:82, and
$R_5-R_6-R_7$ is C-Y-P-P-G-C (SEQ ID NO:181).
In compounds 705–768:
$R_1-R_2-R_3$ is F-E-C,
$R_4$ is one of SEQ ID NO:19–SEQ ID NO:82, and
$R_5-R_6-R_7$ is C-Y-M-D-V (SEQ ID NO:182).
In compounds 769–832:
$R_1-R_2-R_3$ is F-E-C,
$R_4$ is one of SEQ ID NO:19–SEQ ID NO:82, and
$R_5-R_6-R_7$ is Y-F.
In compounds 833–896:
$R_1-R_2-R_3$ is F-E-C,
$R_4$ is one of SEQ ID NO:19–SEQ ID NO:82, and
$R_5-R_6-R_7$ is C-F-D-V (SEQ ID NO:183).
In compounds 897–960:
$R_1-R_2-R_3$ is F-E-C,
$R_4$ is one of SEQ ID NO:19–SEQ ID NO:82, and
$R_5-R_6-R_7$ is C-Y.
In compounds 961–1024:
$R_1-R_2-R_3$ is Y-E-C,
$R_4$ is one of SEQ ID NO:19–SEQ ID NO:82, and
$R_5-R_6-R_7$ is C-Y-P-P-G-C (SEQ ID NO:181).
In compounds 1025–1088:
$R_1-R_2-R_3$ is Y-E-C,
$R_4$ is one of SEQ ID NO:19–SEQ ID NO:82, and
$R_5-R_6-R_7$ is C-Y-M-D-V (SEQ ID NO:182).
In compounds 1089–1152:
$R_1-R_2-R_3$ is Y-E-C,
$R_4$ is one of SEQ ID NO:19–SEQ ID NO:82, and
$R_5-R_6-R_7$ is Y-F.
In compounds 1153–1216:
$R_1-R_2-R_3$ is Y-E-C,
$R_4$ is one of SEQ ID NO:19–SEQ ID NO:82, and
$R_5-R_6-R_7$ is C-F-D-V (SEQ ID NO:183).
In compounds 1217–1280:
$R_1-R_2-R_3$ is Y-E-C,
$R_4$ is one of SEQ ID NO:19–SEQ ID NO:82, and
$R_5-R_6-R_7$ is C-Y.
In some preferred embodiment the compound is F-C-G-D-G-F-Y-A-C-Y-M-D-V (SEQ ID NO:184).

Those having ordinary skill in the art can readily construct molecules according to the above formulae and determine whether or not the compounds are active as p185 binding compounds which prevent and eliminate the p185-mediated transformation phenotype.

The peptides of the invention may be dimerized with each other to form homodimers or with other compounds including compounds of the invention to form heterodimers. In preferred dimers, the residues involved in the chemical bound which links the monomers is in the $R_1$ position of the compounds of the invention.

The compositions used in the method of treating, preventing or imaging tumors or quantifying p185 may comprise mimetics instead of peptides. As used herein, the term "Mimetics" is used to refer to compounds which mimic the activity of peptide. Mimetics are non-peptides but may comprise amino acids linked by non-peptide bonds. Parent application U.S. application Ser. No. 07/940,654 filed Sep. 3, 1992 and parent applications thereof, all of which are incorporated herein by reference, contain detailed guidance on the production of mimetics. Briefly, the three dimensional structure of the peptides which specifically interacts with the three dimensional structure of the p185 is duplicated by a molecule that is not a peptide.

The compounds of the invention may be used to treat individuals suffering from p185-associated tumors. According to one aspect of the invention, compounds are administered to individuals suspected of having p185 tumors. Those having ordinary skill in the art can readily determine whether an individual may have a tumor likely to be a p185 associated tumor. Biopsy protocols can be performed to identify tumor samples and determine whether or not they are p185 associated tumors. The diagnostic/characterization protocol described above may be used in the characterization and determination of p185 levels present on cell samples.

The compounds of the invention may be used to prevent the occurrence of p185 associated tumors in individuals susceptible to p185-associated tumors. According to one aspect of the invention, compounds are administered prophylactically to individuals susceptible to developing p185 tumors. Those having ordinary skill in the art can readily determine whether an individual may be susceptible to p185 associated tumors. The invention is particularly useful in high risk individuals who, for example, have a family history of erbB-2-associated cancer or show a genetic predisposition. Additionally, the present invention is particularly useful to prevent patients who have had erbB-2-associated tumors removed by surgical resection or who have been diagnosed as having erbB-2-associated cancer in remission.

Methods of the present invention comprise administering a single or multiple doses of the compounds of the invention. Preferred for human pharmaceutical use are pharmaceutical compositions that comprise the compounds of the present invention in combination with a pharmaceutically acceptable carrier or diluent.

The pharmaceutical compositions of the present invention may be administered by any means that enables the active agent to reach the agent's site of action in the body of a mammal. In the case of the peptides of the invention, the primary focus is the ability to reach and bind with cellular p185. Because proteins are subject to being digested when administered orally, parenteral administration, i.e., intravenous, subcutaneous, intramuscular, would ordinarily be used to optimize absorption. These small compact forms are resistant to many proteases and should be orally available.

In addition to pharmaceutical compositions which comprise compounds of the invention alone or in combination with other cancer therapeutics, therapeutic and diagnostic pharmaceutical compositions of the present invention include conjugated compounds specifically targeted to p185. The pharmaceutical compositions which comprise conjugated compositions of the present invention may be used to diagnose or treat individuals suffering from p185-associated cancer.

One aspect of the present invention relies upon the use of a compound of the invention conjugated to a detectable and/or cytotoxic agent. In conjugated compositions, the compound of the invention delivers the active agent to cells that have p185. Thus, cells which overexpress p185 will be contacted with more active agents than other cells. The active agent is useful to image, inhibit proliferation of and/or kill the cell. According to one aspect of the present invention, the active agent is a therapeutic agent or an imaging agent.

Some chemotherapeutic agents may be used as active agents and conjugated with compounds of the invention. Chemotherapeutics are typically, small chemical entities produced by chemical synthesis and include cytotoxic drugs, cytostatic drugs as well as compounds which affects cells in other ways such as reversal of the transformed state to a differentiated state or those which inhibit cell replication. Examples of chemotherapeutics include, but are not limited to: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin.

Active agents may be toxins: complex toxic products of various organisms including bacteria, plants, etc. Examples of toxins include but are not limited to: ricin, ricin A chain (ricin toxin), Pseudomonas exotoxin (PE), diphtheria toxin (DT), Clostridium perfringens phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. Protein toxins may be produced using recombinant DNA techniques as fusion proteins which include peptides of the invention. Protein toxins may also be conjugated to compounds of the invention by non-peptidyl bonds.

Radioisotopes may be conjugated to compounds of the invention to provide compositions that are useful as therapeutic agents or for imaging procedures. Examples of radioisotopes which useful in radiation therapy include: $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb and $^{212}$Bi. Example of radioisotopes useful in imaging procedures include: $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi.

Imaging agents are useful in diagnostic procedures as well as the procedures used to identify the location of p185 associated tumors. Imaging can be performed by many procedures well-known to those having ordinary skill in the art and the appropriate imaging agent useful in such procedures may be conjugated to compounds of the invention by well-known means. Imaging can be performed, for example, by radioscintigraphy, nuclear magnetic resonance imaging (MRI) or computed tomography (CT scan). The most commonly employed radiolabels for imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium.

Radiolabels are conjugated to compounds of the invention by a variety of well-known techniques readily performed without undue experimentation by those having ordinary skill in the art. Radiolabels retain their radioactivity irrespective of conjugation. Conjugation may be accomplished directly between the compound and the radioisotope or linking, intermediate molecular groups may be provided between the compound and the radioisotope. Crosslinkers are particularly useful to facilitate conjugation by providing attachment sites for each moiety. Crosslinkers may include additional molecular groups which serve as spacers to separate the moieties from each other to prevent either from interfering with the activity of the other. Often imaging can be imaged using fluorescein, which are activated by light. (e.g. fluorescein (green), phycoerythrin (orange), P-E-cyanine-5 (red), P-E-texas red (red), cyanine-3 (orange), cyananine-5 (red), AMCA (ultraviolet detection)

One having ordinary skill in the art may conjugate a compound of the invention to a chemotherapeutic drug using well-known techniques. For example, Magerstadt, M. *Antibody Conjugates and Malignant Disease*. (1991) CRC Press, Boca Raton, USA, pp. 110–152) which is incorporated herein by reference, teaches the conjugation of various cytostatic drugs to amino acids of antibodies. Such reactions may be applied to conjugate chemotherapeutic drugs to the compounds of the invention. Compounds of the invention such as peptides which have a free amino group may be conjugated to active agents at that group. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of a compound of the invention.

Pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

Because conjugated compounds are specifically targeted to cells with p185, conjugated compounds which comprise chemotherapeutics or toxins are administered in doses less than those which are used when the chemotherapeutics or toxins are administered as unconjugated active agents, preferably in doses that contain up to 100 times less active agent. In some embodiments, conjugated compounds which comprise chemotherapeutics or toxins are administered in doses that contain 10–100 times less active agent as an active agent than the dosage of chemotherapeutics or toxins administered as unconjugated active agents. To determine the appropriate dose, the amount of compound is preferably measured in moles instead of by weight. In that way, the variable weight of different compounds of the invention does not affect the calculation. Presuming a one to one ratio of p185-binding compound to active agent in conjugated compositions of the invention, less moles of conjugated compounds may be administered as compared to the moles of unconjugated compounds administered, preferably up to 100 times less moles.

For parenteral administration, the compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field.

For example, a parenteral composition suitable for administration by injection is prepared by dissolving 1.5% by weight of active ingredient in 0.9% sodium chloride solution.

According to the present invention, the compound may be administered to tissue of an individual by topically or by lavage. The compounds may be formulated as a cream, ointment, salve, douche, suppository or solution for topical administration or irrigation. Formulations for such routes administration of pharmaceutical compositions are well known.

Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations according to the present invention are preferably provided sterile and pyrogen free.

One of skill in the art of pharmaceutical formulations, e.g., having an advanced degree in Pharmaceutics or Pharmaceutical Sciences, can prepare a variety of appropriate dosage forms and formulations for the compositions of the invention with no more than routine experimentation. A number of texts in the field, a,g., *Remington's Pharmaceutical Sciences and The U.S. Pharmacopoeia/National Formulary*, latest editions, provide considerable guidance in this respect.

A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

The compositions may include additional components to render them more effective. For example, a composition of the invention may comprise multiple anti-p185 compounds. The compositions may include other anti-cancer agents such as, for example, cis-platin, methotrexate, and/or G-MCSF. Such compositions would be particularly useful for administration to patients diagnosed and treated for erbB-2-associated cancer. Administration regimen About 5 $\mu$g to 5000 mg of peptide may be administered. In some preferred embodiments, 50 $\mu$g to 500 mg of peptide may be administered. In other preferred embodiments, 500 $\mu$g to 50 mg of peptide may be administered. In a preferred embodiment, 5 mg of peptide is administered.

Prophylactic compositions may be administered by an appropriate route such as, for example, by oral, intranasal, intramuscular, intraperitoneal or subcutaneous administration. In some embodiments, intravenous administration is preferred.

Subsequent to initial administration, individuals may be boosted by readministration. In some preferred embodiments, multiple administrations are performed.

We claim:

1. A method of detecting a tumor that has p185 on tumor cell surfaces comprising the steps of (a) administering, to an individual suspected of having such a tumor or being susceptible to such a tumor, a peptide; and (b) detecting the presence of localized peptide within the body of said individual; said peptide having 10–15 amino acid residues and having the formula:

$$R_1—R_2—R_3—R_4—R_5—R_6—R_7$$

wherein:
- $R_1$ is Phe-Glu, Tyr-Glu, Phe or Tyr;
- $R_2$ is cysteine;
- $R_3$ is 0 amino acids;
- $R_4$ is 6 amino acids;
- $R_5$ is 0 amino acids;
- $R_6$ is cysteine;
- $R_7$ is Phe, Tyr, SEO ID No: 83 or SEQ ID No. 84;

and $R_4$ has the formula:

$$R_{41}—R_{42}—R_{43}—R_{44}—R_{45}—R_{46};$$

wherein:
either
- $R_{41}$ is Glu or Asp;
- $R_{42}$ is Asn or Gln;
- $R_{43}$ is Trp;
- $R_{44}$ is Asp or Glu;
- $R_{45}$ is Trp; and
- $R_{46}$ is Tyr or Phe;

or
- $R_{41}$ is Gly, Val, Ala, Ile or Leu;
- $R_{42}$ is Asp or Glu;
- $R_{43}$ is Gly, Val, Ala, Ile or Leu;
- $R_{44}$ is Phe or Tyr;
- $R_{45}$ is Tyr or Phe; and
- $R_{66}$ is Ala, Ile, Leu, Gly or Val.

2. The method of claim 1 wherein said peptide is linked to a detectable agent.

3. The method of claim 2 wherein the detectable agent is a radioisotope.

4. The method of claim 1 wherein $R_4$ of said peptide has an amino acid sequence selected from the group consisting of SEQ ID NOS: 2–17.

5. The method of claim 1 wherein $R_4$ of said peptize has the amino acid sequence of SEQ ID NO: 2.

6. The method of claim 1 wherein $R_4$ of said peptide has an amino acid sequence selected from the group consisting of SEQ ID NOS: 18–82.

7. The method of claim 6 wherein $R_4$ of said peptide has the amino acid sequence of SEQ ID NO: 19.

8. The method of claim 1 wherein said peptide has the amino acid sequence of SEQ ID NO: 85.

9. The method of claim 1 wherein said peptide has the amino acid sequence of SEQ ID NO: 184.

10. A method of detecting a tumor cell that expresses p185 in a test sample comprising the steps of (a) contacting the test sample with a peptide; and (b) detecting the peptide bound to a cell in the test sample; said peptide having 10–15 amino acid residues and having the formula:

$$R_1-R_2-R_3-R_4-R_5-R_6-R_7$$

wherein:

$R_1$ is Phe-Glu, Tyr-Glu, Phe or Tyr;

$R_2$ is cysteine;

$R_3$ is 0 amino acids;

$R_4$ is 6 amino acids;

$R_5$ is 0 amino acids;

$R_6$ is cysteine;

$R_7$ is Phe, Tyr, SEQ ID No: 83 or SEQ ID No. 84;

and $R_4$ has the formula:

$$R_{41}-R_{42}-R_{43}-R_{44}-R_{45}-R_{46};$$

wherein:
either
$R_{41}$ is Glu or Asp;
$R_{42}$ is Asn or Gln;
$R_{43}$ is Trp;
$R_{44}$ is Asp or Glu;
$R_{45}$ is Trp; and
$R_{46}$ is Tyr or Phe;
or
$R_{41}$ is Gly, Val, Ala, Ile or Leu;
$R_{42}$ is Asp or Glu;
$R_{43}$ is Gly, Val, Ala, Ile or Leu;
$R_{44}$ is Phe or Tyr;
$R_{45}$ is Tyr or Phe; and
$R_{46}$ is Ala, Ile, Leu, Gly or Val.

11. The method of claim 10 wherein said peptide is linked to a detectable agent.

12. The method of claim 11 wherein the detectable agent is a radioisotope.

13. The method of claim 10 wherein $R_4$ of said peptide has an amino acid sequence selected from the group consisting of SEQ ID NOS: 2–17.

14. The method of claim 10 wherein $R_4$ of said peptide has the amino acid sequence of SEQ ID NO: 2.

15. The method of claim 10 wherein $R_4$ of said peptide has an amino acid sequence selected from the group consisting of SEQ ID NOS: 18–82.

16. The method of claim 15 wherein $R_4$ of said peptide has the amino acid sequence of SEQ ID NO: 19.

17. The method of claim 10 wherein said peptide has the amino acid sequence of SEQ ID NO: 85.

18. The method of claim 10 wherein said peptide has the amino acid sequence of SEQ ID NO: 184.

* * * * *

SEQUENCE LISTING (1) GENERAL INFORMATION:

(iii) NUMBER OF SEQUENCES: 184

(2) INFORMATION FOR SEQ ID NO:1:

(i) SEQUENCE CHARACTERISTICS:
      (A) LENGTH: 5
      (B) TYPE: amino acid
      (D) TOPOLOGY: unknown (ii) MOLECULE TYPE: peptide (xi) SEQUENCE DESCRIPTION: SEQ ID NO:1:

Phe Lys Thr Asn Lys
1             5

(2) INFORMATION FOR SEQ ID NO:2:

(i) SEQUENCE CHARACTERISTICS:
      (A) LENGTH: 6
      (B) TYPE: amino acid
      (D) TOPOLOGY: unknown (ii) MOLECULE TYPE:  peptide (xi) SEQUENCE DESCRIPTION: SEQ ID NO:2:

Glu Asn Trp Asp Trp Tyr
1               5

(2) INFORMATION FOR SEQ ID NO:3:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:3:

Asp Asn Trp Asp Trp Tyr
1               5

(2) INFORMATION FOR SEQ ID NO:4:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:4:

Glu Gln Trp Asp Trp Tyr
1               5

(2) INFORMATION FOR SEQ ID NO:5:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:5:

Asp Gln Trp Asp Trp Tyr
1               5

(2) INFORMATION FOR SEQ ID NO:6:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:6:

Glu Asn Trp Glu Trp Tyr
1               5

(2) INFORMATION FOR SEQ ID NO:7:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:7:

Asp Asn Trp Glu Trp Tyr
1               5

(2) INFORMATION FOR SEQ ID NO:8:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:8:

Glu Gln Trp Glu Trp Tyr
1               5

(2) INFORMATION FOR SEQ ID NO:9:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:9:

Asp Gln Trp Glu Trp Tyr
1               5

(2) INFORMATION FOR SEQ ID NO:10:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:10:

Glu Asn Trp Asp Trp Phe
1               5

(2) INFORMATION FOR SEQ ID NO:11:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:11:

Asp Asn Trp Asp Trp Phe
1               5

(2) INFORMATION FOR SEQ ID NO:12:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:12:

Glu Gln Trp Asp Trp Phe
1               5

(2) INFORMATION FOR SEQ ID NO:13:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:13:

Asp Gln Trp Asp Trp Phe
1               5

(2) INFORMATION FOR SEQ ID NO:14:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:14:

Glu Asn Trp Glu Trp Phe
1               5

(2) INFORMATION FOR SEQ ID NO:15:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:15:

Asp Asn Trp Glu Trp Phe
1               5

(2) INFORMATION FOR SEQ ID NO:16:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:16:

Glu Gln Trp Glu Trp Phe
1               5

(2) INFORMATION FOR SEQ ID NO:17:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:17:

Asp Gln Trp Glu Trp Phe
1               5

(2) INFORMATION FOR SEQ ID NO:18:

(i) SEQUENCE CHARACTERISTICS:
            (A) LENGTH: 6 amino acids
            (B) TYPE: amino acid
            (D) TOPOLOGY: unknown (ii) MOLECULE TYPE: peptide (ix) FEATURE:
             (A) NAME/KEY: Modified-site
             (B) LOCATION: 1
             (D) OTHER INFORMATION: /note= "Xaa at position 1 is Gly,
                 Val, Ala, Ile or Leu"

(ix) FEATURE:
             (A) NAME/KEY: Modified-site
             (B) LOCATION: 2
             (D) OTHER INFORMATION: /note= "Xaa at position 2 is Asp or
                 Glu"

(ix) FEATURE:
             (A) NAME/KEY: Modified-site
             (B) LOCATION: 3
             (D) OTHER INFORMATION: /note= "Xaa at position 3 is Gly,
                 Val, Ala, Ile or Leu"

(ix) FEATURE:
             (A) NAME/KEY: Modified-site
             (B) LOCATION: 4
             (D) OTHER INFORMATION: /note= "Xaa at position 4 is Phe or
                 Tyr"

(ix) FEATURE:
             (A) NAME/KEY: Modified-site
             (B) LOCATION: 5
             (D) OTHER INFORMATION: /note= "Xaa at position 5 is Tyr or
                 Phe"

(ix) FEATURE:
             (A) NAME/KEY: Modified-site
             (B) LOCATION: 6
             (D) OTHER INFORMATION: /note= "Xaa at position 6 is Ala, Gly,
                 Val, Ile or Leu"

(xi) SEQUENCE DESCRIPTION: SEQ ID NO:18:

Xaa Xaa Xaa Xaa Xaa Xaa
1               5

(2) INFORMATION FOR SEQ ID NO:19:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:19:

Gly Asp Gly Phe Tyr Ala
1               5

(2) INFORMATION FOR SEQ ID NO:20:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:20:

Gly Glu Gly Phe Tyr Ala
1               5

(2) INFORMATION FOR SEQ ID NO:21:

(i) SEQUENCE CHARACTERISTICS:
            (A) LENGTH:  6
            (B) TYPE:  amino acid (D) TOPOLOGY:  unknown (ii) MOLECULE TYPE:  peptide (xi) SEQUENCE DESCRIPTION: SEQ ID NO:21:

Gly Asp Gly Tyr Tyr Ala
1               5

(2) INFORMATION FOR SEQ ID NO:22:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:22:

Gly Glu Gly Tyr Tyr Ala
1               5

(2) INFORMATION FOR SEQ ID NO:23:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:23:

Gly Asp Gly Phe Phe Ala
1               5

(2) INFORMATION FOR SEQ ID NO:24:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:24:

Gly Glu Gly Phe Phe Ala
1               5

(2) INFORMATION FOR SEQ ID NO:25:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:25:

Gly Asp Gly Tyr Phe Ala
1               5

(2) INFORMATION FOR SEQ ID NO:26:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:26:

Gly Glu Gly Tyr Phe Ala
1               5

(2) INFORMATION FOR SEQ ID NO:27:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:27:

Ala Asp Gly Phe Tyr Ala
1               5

(2) INFORMATION FOR SEQ ID NO:28:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:28:

Ala Glu Gly Phe Tyr Ala
1               5

(2) INFORMATION FOR SEQ ID NO:29:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:29:

Ala Asp Gly Tyr Tyr Ala
1               5

(2) INFORMATION FOR SEQ ID NO:30:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:30:

Ala Glu Gly Tyr Tyr Ala
1               5

(2) INFORMATION FOR SEQ ID NO:31:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:31:

Ala Asp Gly Phe Phe Ala
1               5

(2) INFORMATION FOR SEQ ID NO:32:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:32:

Ala Glu Gly Phe Phe Ala
1          5

(2) INFORMATION FOR SEQ ID NO:33:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:33:

Ala Asp Gly Tyr Phe Ala
1          5

(2) INFORMATION FOR SEQ ID NO:34:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:34:

Ala Glu Gly Tyr Phe Ala
1          5

(2) INFORMATION FOR SEQ ID NO:35:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:35:

Gly Asp Ala Phe Tyr Ala
1          5

(2) INFORMATION FOR SEQ ID NO:36:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:36:

Gly Glu Ala Phe Tyr Ala
1          5

(2) INFORMATION FOR SEQ ID NO:37:

(i) SEQUENCE CHARACTERISTICS:
        (A) LENGTH: 6
        (B) TYPE: amino acid (D) TOPOLOGY:  unknown (ii) MOLECULE TYPE:  peptide (xi) SEQUENCE DESCRIPTION: SEQ ID NO:37:

Gly Asp Ala Tyr Tyr Ala
1               5

(2) INFORMATION FOR SEQ ID NO:38:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:38:

Gly Glu Ala Tyr Tyr Ala
1               5

(2) INFORMATION FOR SEQ ID NO:39:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:39:

Gly Asp Ala Phe Phe Ala
1               5

(2) INFORMATION FOR SEQ ID NO:40:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:40:

Gly Glu Ala Phe Phe Ala
1               5

(2) INFORMATION FOR SEQ ID NO:41:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:41:

Gly Asp Ala Tyr Phe Ala
1               5

(2) INFORMATION FOR SEQ ID NO:42:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:42:

Gly Glu Ala Tyr Phe Ala
1               5

(2) INFORMATION FOR SEQ ID NO:43:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:43:

Ala Asp Ala Phe Tyr Ala
1               5

(2) INFORMATION FOR SEQ ID NO:44:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:44:

Ala Glu Ala Phe Tyr Ala
1               5

(2) INFORMATION FOR SEQ ID NO:45:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:45:

Ala Asp Ala Tyr Tyr Ala
1               5

(2) INFORMATION FOR SEQ ID NO:46:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:46:

Ala Glu Ala Tyr Tyr Ala
1               5

(2) INFORMATION FOR SEQ ID NO:47:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:47:

Ala Asp Ala Phe Phe Ala
1               5

(2) INFORMATION FOR SEQ ID NO:48:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:48:

```
Ala Glu Ala Phe Phe Ala
1               5
```

(2) INFORMATION FOR SEQ ID NO:49:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:49:

```
Ala Asp Ala Tyr Phe Ala
1               5
```

(2) INFORMATION FOR SEQ ID NO:50:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:50:

```
Ala Glu Ala Tyr Phe Ala
1               5
```

(2) INFORMATION FOR SEQ ID NO:51:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:51:

```
Gly Asp Gly Phe Tyr Gly
1               5
```

(2) INFORMATION FOR SEQ ID NO:52:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:52:

```
Gly Glu Gly Phe Tyr Gly
1               5
```

(2) INFORMATION FOR SEQ ID NO:53:

(i) SEQUENCE CHARACTERISTICS:
        (A) LENGTH: 6
        (B) TYPE: amino acid (D) TOPOLOGY:  unknown (ii) MOLECULE TYPE:  peptide (xi) SEQUENCE DESCRIPTION: SEQ ID NO:53:

Gly Asp Gly Tyr Tyr Gly
1               5

(2) INFORMATION FOR SEQ ID NO:54:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:54:

Gly Glu Gly Tyr Tyr Gly
1               5

(2) INFORMATION FOR SEQ ID NO:55:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:55:

Gly Asp Gly Phe Phe Gly
1               5

(2) INFORMATION FOR SEQ ID NO:56:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:56:

Gly Glu Gly Phe Phe Gly
1               5

(2) INFORMATION FOR SEQ ID NO:57:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:57:

Gly Asp Gly Tyr Phe Gly
1               5

(2) INFORMATION FOR SEQ ID NO:58:

(i) SEQUENCE CHARACTERISTICS:
            (A) LENGTH:  6
            (B) TYPE:  amino acid
            (D) TOPOLOGY:  unknown (ii) MOLECULE TYPE:  peptide (xi) SEQUENCE DESCRIPTION: SEQ ID NO:58:

Gly Glu Gly Tyr Phe Gly
1               5

(2) INFORMATION FOR SEQ ID NO:59:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:59:

Ala Asp Gly Phe Tyr Gly
1               5

(2) INFORMATION FOR SEQ ID NO:60:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:60:

Ala Glu Gly Phe Tyr Gly
1               5

(2) INFORMATION FOR SEQ ID NO:61:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:61:

Ala Asp Gly Tyr Tyr Gly
1               5

(2) INFORMATION FOR SEQ ID NO:62:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:62:

Ala Glu Gly Tyr Tyr Gly
1               5

(2) INFORMATION FOR SEQ ID NO:63:

(i) SEQUENCE CHARACTERISTICS:
        (A) LENGTH: 6
        (B) TYPE: amino acid
        (D) TOPOLOGY: unknown (ii) MOLECULE TYPE: peptide (xi) SEQUENCE DESCRIPTION: SEQ ID NO:63:

Ala Asp Gly Phe Phe Gly
1               5

(2) INFORMATION FOR SEQ ID NO:64:

(i) SEQUENCE CHARACTERISTICS:
       (A) LENGTH: 6
       (B) TYPE: amino acid
       (D) TOPOLOGY: unknown (ii) MOLECULE TYPE: peptide (xi) SEQUENCE DESCRIPTION: SEQ ID NO:64:

Ala Glu Gly Phe Phe Gly
1               5

(2) INFORMATION FOR SEQ ID NO:65:

(i) SEQUENCE CHARACTERISTICS:
       (A) LENGTH: 6
       (B) TYPE: amino acid
       (D) TOPOLOGY: unknown (ii) MOLECULE TYPE: peptide (xi) SEQUENCE DESCRIPTION: SEQ ID NO:65:

Ala Asp Gly Tyr Phe Gly
1               5

(2) INFORMATION FOR SEQ ID NO:66:

(i) SEQUENCE CHARACTERISTICS:
       (A) LENGTH: 6
       (B) TYPE: amino acid
       (D) TOPOLOGY: unknown (ii) MOLECULE TYPE: peptide (xi) SEQUENCE DESCRIPTION: SEQ ID NO:66:

Ala Glu Gly Tyr Phe Gly
1               5

(2) INFORMATION FOR SEQ ID NO:67:

(i) SEQUENCE CHARACTERISTICS:
       (A) LENGTH: 6
       (B) TYPE: amino acid
       (D) TOPOLOGY: unknown (ii) MOLECULE TYPE: peptide (xi) SEQUENCE DESCRIPTION: SEQ ID NO:67:

Gly Asp Ala Phe Tyr Gly
1               5

(2) INFORMATION FOR SEQ ID NO:68:

(i) SEQUENCE CHARACTERISTICS:
       (A) LENGTH: 6
       (B) TYPE: amino acid
       (D) TOPOLOGY: unknown (ii) MOLECULE TYPE: peptide (xi) SEQUENCE DESCRIPTION: SEQ ID NO:68:

Gly Glu Ala Phe Tyr Gly
1               5

(2) INFORMATION FOR SEQ ID NO:69:

(i) SEQUENCE CHARACTERISTICS:
       (A) LENGTH: 6
       (B) TYPE: amino acid (D) TOPOLOGY: unknown (ii) MOLECULE TYPE: peptide (xi) SEQUENCE DESCRIPTION: SEQ ID NO:69:

Gly Asp Ala Tyr Tyr Gly
1               5

(2) INFORMATION FOR SEQ ID NO:70:

(i) SEQUENCE CHARACTERISTICS:
      (A) LENGTH: 6
      (B) TYPE: amino acid
      (D) TOPOLOGY: unknown (ii) MOLECULE TYPE: peptide (xi) SEQUENCE DESCRIPTION: SEQ ID NO:70:

Gly Glu Ala Tyr Tyr Gly
1               5

(2) INFORMATION FOR SEQ ID NO:71:

(i) SEQUENCE CHARACTERISTICS:
      (A) LENGTH: 6
      (B) TYPE: amino acid
      (D) TOPOLOGY: unknown (ii) MOLECULE TYPE: peptide (xi) SEQUENCE DESCRIPTION: SEQ ID NO:71:

Gly Asp Ala Phe Phe Gly
1               5

(2) INFORMATION FOR SEQ ID NO:72:

(i) SEQUENCE CHARACTERISTICS:
      (A) LENGTH: 6
      (B) TYPE: amino acid
      (D) TOPOLOGY: unknown (ii) MOLECULE TYPE: peptide (xi) SEQUENCE DESCRIPTION: SEQ ID NO:72:

Gly Glu Ala Phe Phe Gly
1               5

(2) INFORMATION FOR SEQ ID NO:73:

(i) SEQUENCE CHARACTERISTICS:
      (A) LENGTH: 6
      (B) TYPE: amino acid
      (D) TOPOLOGY: unknown (ii) MOLECULE TYPE: peptide (xi) SEQUENCE DESCRIPTION: SEQ ID NO:73:

Gly Asp Ala Tyr Phe Gly
1               5

(2) INFORMATION FOR SEQ ID NO:74:

(i) SEQUENCE CHARACTERISTICS:
      (A) LENGTH: 6
      (B) TYPE: amino acid
      (D) TOPOLOGY: unknown (ii) MOLECULE TYPE: peptide (xi) SEQUENCE DESCRIPTION: SEQ ID NO:74:

Gly Glu Ala Tyr Phe Gly
1               5

(2) INFORMATION FOR SEQ ID NO:75:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:75:

Ala Asp Ala Phe Tyr Gly
1               5

(2) INFORMATION FOR SEQ ID NO:76:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:76:

Ala Glu Ala Phe Tyr Gly
1               5

(2) INFORMATION FOR SEQ ID NO:77:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:77:

Ala Asp Ala Tyr Tyr Gly
1               5

(2) INFORMATION FOR SEQ ID NO:78:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:78:

Ala Glu Ala Tyr Tyr Gly
1               5

(2) INFORMATION FOR SEQ ID NO:79:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:79:

Ala Asp Ala Phe Phe Gly
1               5

(2) INFORMATION FOR SEQ ID NO:80:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:80:

Ala Glu Ala Phe Phe Gly
1           5

(2) INFORMATION FOR SEQ ID NO:81:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:81:

Ala Asp Ala Tyr Phe Gly
1           5

(2) INFORMATION FOR SEQ ID NO:82:

(i) SEQUENCE CHARACTERISTICS:
        (A) LENGTH:  6
        (B) TYPE:  amino acid
        (D) TOPOLOGY:  unknown (ii) MOLECULE TYPE:  peptide (xi) SEQUENCE DESCRIPTION: SEQ ID NO:82:

Ala Glu Ala Tyr Phe Gly
1           5

(2) INFORMATION FOR SEQ ID NO:83:

(i) SEQUENCE CHARACTERISTICS:
        (A) LENGTH:  5
        (B) TYPE:  amino acid
        (D) TOPOLOGY:  unknown (ii) MOLECULE TYPE:  peptide (xi) SEQUENCE DESCRIPTION: SEQ ID NO:83:

Tyr Pro Pro Gly Cys
1           5

(2) INFORMATION FOR SEQ ID NO:84:

(i) SEQUENCE CHARACTERISTICS:
        (A) LENGTH:  4
        (B) TYPE:  amino acid
        (D) TOPOLOGY:  unknown (ii) MOLECULE TYPE:  peptide (xi) SEQUENCE DESCRIPTION: SEQ ID NO:84:

Tyr Met Asp Val
1

(2) INFORMATION FOR SEQ ID NO:85:

(i) SEQUENCE CHARACTERISTICS:
        (A) LENGTH:  15
        (B) TYPE:  amino acid (D) TOPOLOGY: unknown (ii) MOLECULE TYPE: peptide (xi) SEQUENCE DESCRIPTION: SEQ ID NO:85:

Phe Glu Cys Glu Asn Trp Asp Trp Tyr Cys Tyr Pro Pro Gly Cys
1               5                  10                  15

(2) INFORMATION FOR SEQ ID NO:86:

(i) SEQUENCE CHARACTERISTICS:
        (A) LENGTH: 12
        (B) TYPE: amino acid
        (D) TOPOLOGY: unknown (ii) MOLECULE TYPE: peptide (xi) SEQUENCE DESCRIPTION: SEQ ID NO:86:

Phe Cys Gly Asp Gly Phe Tyr Ala Cys Met Asp Val
1               5                  10

(2) INFORMATION FOR SEQ ID NO:87:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:87:

Phe Glu Cys Asp Asn Trp Asp Trp Tyr Cys Tyr Pro Pro Gly Cys
1               5                  10                  15

(2) INFORMATION FOR SEQ ID NO:88:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:88:

Phe Glu Cys Glu Gln Trp Asp Trp Tyr Cys Tyr Pro Pro Gly Cys
1               5                  10                  15

(2) INFORMATION FOR SEQ ID NO:89:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:89:

Phe Glu Cys Asp Gln Trp Asp Trp Tyr Cys Tyr Pro Pro Gly Cys
1               5                  10                  15

(2) INFORMATION FOR SEQ ID NO:90:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:90:

```
Phe Glu Cys Glu Asn Trp Glu Trp Tyr Cys Tyr Pro Pro Gly Cys
1               5                   10                  15
```

(2) INFORMATION FOR SEQ ID NO:91:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:91:

```
Phe Glu Cys Asp Asn Trp Glu Trp Tyr Cys Tyr Pro Pro Gly Cys
1               5                   10                  15
```

(2) INFORMATION FOR SEQ ID NO:92:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:92:

```
Phe Glu Cys Glu Gln Trp Glu Trp Tyr Cys Tyr Pro Pro Gly Cys
1               5                   10                  15
```

(2) INFORMATION FOR SEQ ID NO:93:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:93:

```
Phe Glu Cys Asp Gln Trp Glu Trp Tyr Cys Tyr Pro Pro Gly Cys
1               5                   10                  15
```

(2) INFORMATION FOR SEQ ID NO:94:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:94:

```
Phe Glu Cys Glu Asn Trp Asp Trp Phe Cys Tyr Pro Pro Gly Cys
1               5                   10                  15
```

(2) INFORMATION FOR SEQ ID NO:95:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:95:

```
Phe Glu Cys Asp Asn Trp Asp Trp Phe Cys Tyr Pro Pro Gly Cys
1               5                   10                  15
```

```
(2) INFORMATION FOR SEQ ID NO:96:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:96:

Phe Glu Cys Glu Gln Trp Asp Trp Phe Cys Tyr Pro Pro Gly Cys
1               5                   10                  15

(2) INFORMATION FOR SEQ ID NO:97:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:97:

Phe Glu Cys Asp Gln Trp Asp Trp Phe Cys Tyr Pro Pro Gly Cys
1               5                   10                  15

(2) INFORMATION FOR SEQ ID NO:98:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:98:

Phe Glu Cys Glu Asn Trp Glu Trp Phe Cys Tyr Pro Pro Gly Cys
1               5                   10                  15

(2) INFORMATION FOR SEQ ID NO:99:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:99:

Phe Glu Cys Asp Asn Trp Glu Trp Phe Cys Tyr Pro Pro Gly Cys
1               5                   10                  15

(2) INFORMATION FOR SEQ ID NO:100:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:100:

Phe Glu Cys Glu Gln Trp Glu Trp Phe Cys Tyr Pro Pro Gly Cys
1               5                   10                  15

(2) INFORMATION FOR SEQ ID NO:101:

(i) SEQUENCE CHARACTERISTICS:
        (A) LENGTH:  15
        (B) TYPE:  amino acid
```

(D) TOPOLOGY:  unknown (ii) MOLECULE TYPE:  peptide (xi) SEQUENCE DESCRIPTION: SEQ ID NO:101:

Phe Glu Cys Asp Gln Trp Glu Trp Phe Cys Tyr Pro Pro Gly Cys
1               5                  10                  15

(2) INFORMATION FOR SEQ ID NO:102:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:102:

Phe Cys Glu Asn Trp Asp Trp Tyr Cys Tyr Pro Pro Gly Cys
1               5                  10

(2) INFORMATION FOR SEQ ID NO:103:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:103:

Phe Cys Asp Asn Trp Asp Trp Tyr Cys Tyr Pro Pro Gly Cys
1               5                  10

(2) INFORMATION FOR SEQ ID NO:104:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:104:

Phe Cys Glu Gln Trp Asp Trp Tyr Cys Tyr Pro Pro Gly Cys
1               5                  10

(2) INFORMATION FOR SEQ ID NO:105:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:105:

Phe Cys Asp Gln Trp Asp Trp Tyr Cys Tyr Pro Pro Gly Cys
1               5                  10

(2) INFORMATION FOR SEQ ID NO:106:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:106:

Phe Cys Glu Asn Trp Glu Trp Tyr Cys Tyr Pro Pro Gly Cys
1               5                   10

(2) INFORMATION FOR SEQ ID NO:107:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:107:

Phe Cys Asp Asn Trp Glu Trp Tyr Cys Tyr Pro Pro Gly Cys
1               5                   10

(2) INFORMATION FOR SEQ ID NO:108:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:108:

Phe Cys Glu Gln Trp Glu Trp Tyr Cys Tyr Pro Pro Gly Cys
1               5                   10

(2) INFORMATION FOR SEQ ID NO:109:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:109:

Phe Cys Asp Gln Trp Glu Trp Tyr Cys Tyr Pro Pro Gly Cys
1               5                   10

(2) INFORMATION FOR SEQ ID NO:110:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:110:

Phe Cys Glu Asn Trp Asp Trp Phe Cys Tyr Pro Pro Gly Cys
1               5                   10

(2) INFORMATION FOR SEQ ID NO:111:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:111:

Phe Cys Asp Asn Trp Asp Trp Phe Cys Tyr Pro Pro Gly Cys
1               5                   10

(2) INFORMATION FOR SEQ ID NO:112:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:112:

Phe Cys Glu Gln Trp Asp Trp Phe Cys Tyr Pro Pro Gly Cys
1               5                   10

(2) INFORMATION FOR SEQ ID NO:113:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:113:

Phe Cys Asp Gln Trp Asp Trp Phe Cys Tyr Pro Pro Gly Cys
1               5                   10

(2) INFORMATION FOR SEQ ID NO:114:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:114:

Phe Cys Glu Asn Trp Glu Trp Phe Cys Tyr Pro Pro Gly Cys
1               5                   10

(2) INFORMATION FOR SEQ ID NO:115:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:115:

Phe Cys Asp Asn Trp Glu Trp Phe Cys Tyr Pro Pro Gly Cys
1               5                   10

(2) INFORMATION FOR SEQ ID NO:116:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:116:

Phe Cys Glu Gln Trp Glu Trp Phe Cys Tyr Pro Pro Gly Cys
1               5                   10

(2) INFORMATION FOR SEQ ID NO:117:

(i) SEQUENCE CHARACTERISTICS:
        (A) LENGTH: 14
        (B) TYPE: amino acid (D) TOPOLOGY:  unknown (ii) MOLECULE TYPE:  peptide (xi) SEQUENCE DESCRIPTION: SEQ ID NO:117:

Phe Cys Asp Gln Trp Glu Trp Phe Cys Tyr Pro Pro Gly Cys
1               5                   10

(2) INFORMATION FOR SEQ ID NO:118:

(i) SEQUENCE CHARACTERISTICS:
            (A) LENGTH:  11
            (B) TYPE:  amino acid
            (D) TOPOLOGY:  unknown (ii) MOLECULE TYPE:  peptide (xi) SEQUENCE DESCRIPTION: SEQ ID NO:118:

Phe Glu Cys Glu Asn Trp Asp Trp Tyr Cys Tyr
1               5                   10

(2) INFORMATION FOR SEQ ID NO:119:

(i) SEQUENCE CHARACTERISTICS:
            (A) LENGTH:  11
            (B) TYPE:  amino acid
            (D) TOPOLOGY:  unknown (ii) MOLECULE TYPE:  peptide (xi) SEQUENCE DESCRIPTION: SEQ ID NO:119:

Phe Glu Cys Asp Asn Trp Asp Trp Tyr Cys Tyr
1               5                   10

(2) INFORMATION FOR SEQ ID NO:120:

(i) SEQUENCE CHARACTERISTICS:
            (A) LENGTH:  11
            (B) TYPE:  amino acid
            (D) TOPOLOGY:  unknown (ii) MOLECULE TYPE:  peptide (xi) SEQUENCE DESCRIPTION: SEQ ID NO:120:

Phe Glu Cys Glu Gln Trp Asp Trp Tyr Cys Tyr
1               5                   10

(2) INFORMATION FOR SEQ ID NO:121:

(i) SEQUENCE CHARACTERISTICS:
            (A) LENGTH:  11
            (B) TYPE:  amino acid
            (D) TOPOLOGY:  unknown (ii) MOLECULE TYPE:  peptide (xi) SEQUENCE DESCRIPTION: SEQ ID NO:121:

Phe Glu Cys Asp Gln Trp Asp Trp Tyr Cys Tyr
1               5                   10

(2) INFORMATION FOR SEQ ID NO:122:

(i) SEQUENCE CHARACTERISTICS:
            (A) LENGTH:  11
            (B) TYPE:  amino acid
            (D) TOPOLOGY:  unknown (ii) MOLECULE TYPE:  peptide (xi) SEQUENCE DESCRIPTION: SEQ ID NO:122:

```
Phe Glu Cys Glu Asn Trp Glu Trp Tyr Cys Tyr
1               5                   10
```

(2) INFORMATION FOR SEQ ID NO:123:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:123:

```
Phe Glu Cys Asp Asn Trp Glu Trp Tyr Cys Tyr
1               5                   10
```

(2) INFORMATION FOR SEQ ID NO:124:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:124:

```
Phe Glu Cys Glu Gln Trp Glu Trp Tyr Cys Tyr
1               5                   10
```

(2) INFORMATION FOR SEQ ID NO:125:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:125:

```
Phe Glu Cys Asp Gln Trp Glu Trp Tyr Cys Tyr
1               5                   10
```

(2) INFORMATION FOR SEQ ID NO:126:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:126:

```
Phe Glu Cys Glu Asn Trp Asp Trp Phe Cys Tyr
1               5                   10
```

(2) INFORMATION FOR SEQ ID NO:127:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:127:

```
Phe Glu Cys Asp Asn Trp Asp Trp Phe Cys Tyr
1               5                   10
```

(2) INFORMATION FOR SEQ ID NO:128:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:128:

Phe Glu Cys Glu Gln Trp Asp Trp Phe Cys Tyr
1               5                   10

(2) INFORMATION FOR SEQ ID NO:129:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:129:

Phe Glu Cys Asp Gln Trp Asp Trp Phe Cys Tyr
1               5                   10

(2) INFORMATION FOR SEQ ID NO:130:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:130:

Phe Glu Cys Glu Asn Trp Glu Trp Phe Cys Tyr
1               5                   10

(2) INFORMATION FOR SEQ ID NO:131:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:131:

Phe Glu Cys Asp Asn Trp Glu Trp Phe Cys Tyr
1               5                   10

(2) INFORMATION FOR SEQ ID NO:132:

(i) SEQUENCE CHARACTERISTICS:
        (A) LENGTH: 11
        (B) TYPE: amino acid
        (D) TOPOLOGY: unknown (ii) MOLECULE TYPE: peptide (xi) SEQUENCE DESCRIPTION: SEQ ID NO:132:

Phe Glu Cys Glu Gln Trp Glu Trp Phe Cys Tyr
1               5                   10

(2) INFORMATION FOR SEQ ID NO:133:

(i) SEQUENCE CHARACTERISTICS:
        (A) LENGTH: 11
        (B) TYPE: amino acid (D) TOPOLOGY: unknown (ii) MOLECULE TYPE: peptide (xi) SEQUENCE DESCRIPTION: SEQ ID NO:133:

Phe Glu Cys Asp Gln Trp Glu Trp Phe Cys Tyr
1               5                   10

(2) INFORMATION FOR SEQ ID NO:134:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:134:

Phe Cys Glu Asn Trp Asp Trp Tyr Cys Tyr
1               5                   10

(2) INFORMATION FOR SEQ ID NO:135:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:135:

Phe Cys Asp Asn Trp Asp Trp Tyr Cys Tyr
1               5                   10

(2) INFORMATION FOR SEQ ID NO:136:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:136:

Phe Cys Glu Gln Trp Asp Trp Tyr Cys Tyr
1               5                   10

(2) INFORMATION FOR SEQ ID NO:137:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:137:

Phe Cys Asp Gln Trp Asp Trp Tyr Cys Tyr
1               5                   10

(2) INFORMATION FOR SEQ ID NO:138:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:138:

Phe Cys Glu Asn Trp Glu Trp Tyr Cys Tyr
1               5                   10

(2) INFORMATION FOR SEQ ID NO:139:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:139:

Phe Cys Asp Asn Trp Glu Trp Tyr Cys Tyr
1               5                   10

(2) INFORMATION FOR SEQ ID NO:140:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:140:

Phe Cys Glu Gln Trp Glu Trp Tyr Cys Tyr
1               5                   10

(2) INFORMATION FOR SEQ ID NO:141:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:141:

Phe Cys Asp Gln Trp Glu Trp Tyr Cys Tyr
1               5                   10

(2) INFORMATION FOR SEQ ID NO:142:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:142:

Phe Cys Glu Asn Trp Asp Trp Phe Cys Tyr
1               5                   10

(2) INFORMATION FOR SEQ ID NO:143:

(i) SEQUENCE CHARACTERISTICS:
        (A) LENGTH: 10
        (B) TYPE: amino acid
        (D) TOPOLOGY: unknown (ii) MOLECULE TYPE: peptide (xi) SEQUENCE DESCRIPTION: SEQ ID NO:143:

Phe Cys Asp Asn Trp Asp Trp Phe Cys Tyr
1               5                   10

(2) INFORMATION FOR SEQ ID NO:144:

(i) SEQUENCE CHARACTERISTICS:
        (A) LENGTH:  10
        (B) TYPE:  amino acid
        (D) TOPOLOGY:  unknown (ii) MOLECULE TYPE:  peptide (xi) SEQUENCE DESCRIPTION: SEQ ID NO:144:

```
Phe Cys Glu Gln Trp Asp Trp Phe Cys Tyr
1               5                   10
```

(2) INFORMATION FOR SEQ ID NO:145:

(i) SEQUENCE CHARACTERISTICS:
        (A) LENGTH:  10
        (B) TYPE:  amino acid
        (D) TOPOLOGY:  unknown (ii) MOLECULE TYPE:  peptide (xi) SEQUENCE DESCRIPTION: SEQ ID NO:145:

```
Phe Cys Asp Gln Trp Asp Trp Phe Cys Tyr
1               5                   10
```

(2) INFORMATION FOR SEQ ID NO:146:

(i) SEQUENCE CHARACTERISTICS:
        (A) LENGTH:  10
        (B) TYPE:  amino acid
        (D) TOPOLOGY:  unknown (ii) MOLECULE TYPE:  peptide (xi) SEQUENCE DESCRIPTION: SEQ ID NO:146:

```
Phe Cys Glu Asn Trp Glu Trp Phe Cys Tyr
1               5                   10
```

(2) INFORMATION FOR SEQ ID NO:147:

(i) SEQUENCE CHARACTERISTICS:
        (A) LENGTH:  10
        (B) TYPE:  amino acid
        (D) TOPOLOGY:  unknown (ii) MOLECULE TYPE:  peptide (xi) SEQUENCE DESCRIPTION: SEQ ID NO:147:

```
Phe Cys Asp Asn Trp Glu Trp Phe Cys Tyr
1               5                   10
```

(2) INFORMATION FOR SEQ ID NO:148:

(i) SEQUENCE CHARACTERISTICS:
        (A) LENGTH:  10
        (B) TYPE:  amino acid
        (D) TOPOLOGY:  unknown (ii) MOLECULE TYPE:  peptide (xi) SEQUENCE DESCRIPTION: SEQ ID NO:148:

```
Phe Cys Glu Gln Trp Glu Trp Phe Cys Tyr
1               5                   10
```

(2) INFORMATION FOR SEQ ID NO:149:

(i) SEQUENCE CHARACTERISTICS:
        (A) LENGTH:  10
        (B) TYPE:  amino acid (D) TOPOLOGY:  unknown (ii) MOLECULE TYPE:  peptide (xi) SEQUENCE DESCRIPTION: SEQ ID NO:149:

Phe Cys Asp Gln Trp Glu Trp Phe Cys Tyr
1               5                   10

(2) INFORMATION FOR SEQ ID NO:150:

(i) SEQUENCE CHARACTERISTICS:
            (A) LENGTH:  15
            (B) TYPE:  amino acid
            (D) TOPOLOGY:  unknown (ii) MOLECULE TYPE:  peptide (xi) SEQUENCE DESCRIPTION: SEQ ID NO:150:

Phe Glu Cys Asp Asn Trp Asp Trp Tyr Cys Tyr Pro Pro Gly Cys
1               5                   10                  15

(2) INFORMATION FOR SEQ ID NO:151:

(i) SEQUENCE CHARACTERISTICS:
            (A) LENGTH:  15
            (B) TYPE:  amino acid
            (D) TOPOLOGY:  unknown (ii) MOLECULE TYPE:  peptide (xi) SEQUENCE DESCRIPTION: SEQ ID NO:151:

Phe Glu Cys Glu Gln Trp Asp Trp Tyr Cys Tyr Pro Pro Gly Cys
1               5                   10                  15

(2) INFORMATION FOR SEQ ID NO:152:

(i) SEQUENCE CHARACTERISTICS:
            (A) LENGTH:  15
            (B) TYPE:  amino acid
            (D) TOPOLOGY:  unknown (ii) MOLECULE TYPE:  peptide (xi) SEQUENCE DESCRIPTION: SEQ ID NO:152:

Phe Glu Cys Asp Gln Trp Asp Trp Tyr Cys Tyr Pro Pro Gly Cys
1               5                   10                  15

(2) INFORMATION FOR SEQ ID NO:153:

(i) SEQUENCE CHARACTERISTICS:
            (A) LENGTH:  15
            (B) TYPE:  amino acid
            (D) TOPOLOGY:  unknown (ii) MOLECULE TYPE:  peptide (xi) SEQUENCE DESCRIPTION: SEQ ID NO:153:

Phe Glu Cys Glu Asn Trp Glu Trp Tyr Cys Tyr Pro Pro Gly Cys
1               5                   10                  15

(2) INFORMATION FOR SEQ ID NO:154:

(i) SEQUENCE CHARACTERISTICS:
            (A) LENGTH:  15
            (B) TYPE:  amino acid
            (D) TOPOLOGY:  unknown (ii) MOLECULE TYPE:  peptide (xi) SEQUENCE DESCRIPTION: SEQ ID NO:154:

```
Phe Glu Cys Asp Asn Trp Glu Trp Tyr Cys Tyr Pro Pro Gly Cys
1               5                   10                  15
```

(2) INFORMATION FOR SEQ ID NO:155:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:155:

```
Phe Glu Cys Glu Gln Trp Glu Trp Tyr Cys Tyr Pro Pro Gly Cys
1               5                   10                  15
```

(2) INFORMATION FOR SEQ ID NO:156:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:156:

```
Phe Glu Cys Asp Gln Trp Glu Trp Tyr Cys Tyr Pro Pro Gly Cys
1               5                   10                  15
```

(2) INFORMATION FOR SEQ ID NO:157:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:157:

```
Phe Glu Cys Glu Asn Trp Asp Trp Phe Cys Tyr Pro Pro Gly Cys
1               5                   10                  15
```

(2) INFORMATION FOR SEQ ID NO:158:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:158:

```
Phe Glu Cys Asp Asn Trp Asp Trp Phe Cys Tyr Pro Pro Gly Cys
1               5                   10                  15
```

(2) INFORMATION FOR SEQ ID NO:159:

(i) SEQUENCE CHARACTERISTICS:
        (A) LENGTH: 15
        (B) TYPE: amino acid
        (D) TOPOLOGY: unknown (ii) MOLECULE TYPE: peptide (xi) SEQUENCE DESCRIPTION: SEQ ID NO:159:

```
Phe Glu Cys Glu Gln Trp Asp Trp Phe Cys Tyr Pro Pro Gly Cys
1               5                   10                  15
```

(2) INFORMATION FOR SEQ ID NO:160:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:160:

Phe Glu Cys Asp Gln Trp Asp Trp Phe Cys Tyr Pro Pro Gly Cys
1               5                  10                  15

(2) INFORMATION FOR SEQ ID NO:161:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:161:

Phe Glu Cys Glu Asn Trp Glu Trp Phe Cys Tyr Pro Pro Gly Cys
1               5                  10                  15

(2) INFORMATION FOR SEQ ID NO:162:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:162:

Phe Glu Cys Asp Asn Trp Glu Trp Phe Cys Tyr Pro Pro Gly Cys
1               5                  10                  15

(2) INFORMATION FOR SEQ ID NO:163:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:163:

Phe Glu Cys Glu Gln Trp Glu Trp Phe Cys Tyr Pro Pro Gly Cys
1               5                  10                  15

(2) INFORMATION FOR SEQ ID NO:164:

(i) SEQUENCE CHARACTERISTICS:
        (A) LENGTH:  15
        (B) TYPE:  amino acid
        (D) TOPOLOGY:  unknown (ii) MOLECULE TYPE:  peptide (xi) SEQUENCE DESCRIPTION: SEQ ID NO:164:

Phe Glu Cys Asp Gln Trp Glu Trp Phe Cys Tyr Pro Pro Gly Cys
1               5                  10                  15

(2) INFORMATION FOR SEQ ID NO:165:

(i) SEQUENCE CHARACTERISTICS:
        (A) LENGTH:  14
        (B) TYPE:  amino acid (D) TOPOLOGY:  unknown (ii) MOLECULE TYPE:  peptide (xi) SEQUENCE DESCRIPTION: SEQ ID NO:165:

Phe Cys Glu Asn Trp Asp Trp Tyr Cys Tyr Pro Pro Gly Cys
1               5                   10

(2) INFORMATION FOR SEQ ID NO:166:

(i) SEQUENCE CHARACTERISTICS:
            (A) LENGTH:  14
            (B) TYPE:  amino acid
            (D) TOPOLOGY:  unknown (ii) MOLECULE TYPE:  peptide (xi) SEQUENCE DESCRIPTION: SEQ ID NO:166:

Phe Cys Asp Asn Trp Asp Trp Tyr Cys Tyr Pro Pro Gly Cys
1               5                   10

(2) INFORMATION FOR SEQ ID NO:167:

(i) SEQUENCE CHARACTERISTICS:
            (A) LENGTH:  14
            (B) TYPE:  amino acid
            (D) TOPOLOGY:  unknown (ii) MOLECULE TYPE:  peptide (xi) SEQUENCE DESCRIPTION: SEQ ID NO:167:

Phe Cys Glu Gln Trp Asp Trp Tyr Cys Tyr Pro Pro Gly Cys
1               5                   10

(2) INFORMATION FOR SEQ ID NO:168:

(i) SEQUENCE CHARACTERISTICS:
            (A) LENGTH:  14
            (B) TYPE:  amino acid
            (D) TOPOLOGY:  unknown (ii) MOLECULE TYPE:  peptide (xi) SEQUENCE DESCRIPTION: SEQ ID NO:168:

Phe Cys Asp Gln Trp Asp Trp Tyr Cys Tyr Pro Pro Gly Cys
1               5                   10

(2) INFORMATION FOR SEQ ID NO:169:

(i) SEQUENCE CHARACTERISTICS:
            (A) LENGTH:  14
            (B) TYPE:  amino acid
            (D) TOPOLOGY:  unknown (ii) MOLECULE TYPE:  peptide (xi) SEQUENCE DESCRIPTION: SEQ ID NO:169:

Phe Cys Glu Asn Trp Glu Trp Tyr Cys Tyr Pro Pro Gly Cys
1               5                   10

(2) INFORMATION FOR SEQ ID NO:170:

(i) SEQUENCE CHARACTERISTICS:
            (A) LENGTH:  14
            (B) TYPE:  amino acid
            (D) TOPOLOGY:  unknown (ii) MOLECULE TYPE:  peptide (xi) SEQUENCE DESCRIPTION: SEQ ID NO:170:

Phe Cys Asp Asn Trp Glu Trp Tyr Cys Tyr Pro Pro Gly Cys
1               5                   10

(2) INFORMATION FOR SEQ ID NO:171:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:171:

Phe Cys Glu Gln Trp Glu Trp Tyr Cys Tyr Pro Pro Gly Cys
1               5                   10

(2) INFORMATION FOR SEQ ID NO:172:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:172:

Phe Cys Asp Gln Trp Glu Trp Tyr Cys Tyr Pro Pro Gly Cys
1               5                   10

(2) INFORMATION FOR SEQ ID NO:173:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:173:

Phe Cys Glu Asn Trp Asp Trp Phe Cys Tyr Pro Pro Gly Cys
1               5                   10

(2) INFORMATION FOR SEQ ID NO:174:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:174:

Phe Cys Asp Asn Trp Asp Trp Phe Cys Tyr Pro Pro Gly Cys
1               5                   10

(2) INFORMATION FOR SEQ ID NO:175:

(i) SEQUENCE CHARACTERISTICS:
        (A) LENGTH: 14
        (B) TYPE: amino acid
        (D) TOPOLOGY: unknown (ii) MOLECULE TYPE: peptide (xi) SEQUENCE DESCRIPTION: SEQ ID NO:175:

Phe Cys Glu Gln Trp Asp Trp Phe Cys Tyr Pro Pro Gly Cys
1               5                   10

(2) INFORMATION FOR SEQ ID NO:176:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:176:

```
Phe Cys Asp Gln Trp Asp Trp Phe Cys Tyr Pro Pro Gly Cys
1               5                   10
```

(2) INFORMATION FOR SEQ ID NO:177:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:177:

```
Phe Cys Glu Asn Trp Glu Trp Phe Cys Tyr Pro Pro Gly Cys
1               5                   10
```

(2) INFORMATION FOR SEQ ID NO:178:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:178:

```
Phe Cys Asp Asn Trp Glu Trp Phe Cys Tyr Pro Pro Gly Cys
1               5                   10
```

(2) INFORMATION FOR SEQ ID NO:179:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:179:

```
Phe Cys Glu Gln Trp Glu Trp Phe Cys Tyr Pro Pro Gly Cys
1               5                   10
```

(2) INFORMATION FOR SEQ ID NO:180:

(i) SEQUENCE CHARACTERISTICS:
        (A) LENGTH:  14
        (B) TYPE:  amino acid
        (D) TOPOLOGY:  unknown (ii) MOLECULE TYPE:  peptide (xi) SEQUENCE DESCRIPTION: SEQ ID NO:180:

```
Phe Cys Asp Gln Trp Glu Trp Phe Cys Tyr Pro Pro Gly Cys
1               5                   10
```

(2) INFORMATION FOR SEQ ID NO:181:

(i) SEQUENCE CHARACTERISTICS:
        (A) LENGTH:  6
        (B) TYPE:  amino acid

```
            (D) TOPOLOGY:  unknown (ii) MOLECULE TYPE:  peptide (xi) SEQUENCE DESCRIPTION: SEQ ID NO:181:

Cys Tyr Pro Pro Gly Cys
1               5

(2) INFORMATION FOR SEQ ID NO:182:

(i) SEQUENCE CHARACTERISTICS:
            (A) LENGTH:  5
            (B) TYPE:  amino acid
            (D) TOPOLOGY:  unknown (ii) MOLECULE TYPE:  peptide (xi) SEQUENCE DESCRIPTION: SEQ ID NO:182:

Cys Tyr Met Asp Val
1               5

(2) INFORMATION FOR SEQ ID NO:183:

(i) SEQUENCE CHARACTERISTICS:
            (A) LENGTH:  4
            (B) TYPE:  amino acid
            (D) TOPOLOGY:  unknown (ii) MOLECULE TYPE:  peptide (xi) SEQUENCE DESCRIPTION: SEQ ID NO:183:

Cys Phe Asp Val
1

(2) INFORMATION FOR SEQ ID NO:184:

(i) SEQUENCE CHARACTERISTICS:
            (A) LENGTH:  13
            (B) TYPE:  amino acid
            (D) TOPOLOGY:  unknown (ii) MOLECULE TYPE:  peptide (xi) SEQUENCE DESCRIPTION: SEQ ID NO:184:

Phe Cys Gly Asp Gly Phe Tyr Ala Cys Tyr Met Asp Val
1               5                  10
```